(12) United States Patent
Ingram et al.

(10) Patent No.: US 8,426,800 B2
(45) Date of Patent: Apr. 23, 2013

(54) INTEGRATING OPTICAL SYSTEMS AND METHODS

(75) Inventors: Michael W. Ingram, Austin, TX (US);
Joseph C. Stumpf, Hemet, CA (US);
Jon P. Conway, San Diego, CA (US)

(73) Assignee: Vela Technologies, Inc., San Diego, CA (US)

(*) Notice: Subject to any disclaimer, the term of this patent is extended or adjusted under 35 U.S.C. 154(b) by 47 days.

(21) Appl. No.: 13/229,544

(22) Filed: Sep. 9, 2011

(65) Prior Publication Data

US 2012/0085926 A1 Apr. 12, 2012

Related U.S. Application Data

(60) Provisional application No. 61/381,165, filed on Sep. 9, 2010.

(51) Int. Cl.
*G01J 1/00* (2006.01)
*G01J 1/04* (2006.01)
*G02B 5/02* (2006.01)
*B60Q 1/26* (2006.01)
*F21V 5/00* (2006.01)

(52) U.S. Cl.
USPC ........ 250/228; 250/492.1; 362/227; 362/246; 356/236; 356/244; 356/446

(58) Field of Classification Search .................. 250/228, 250/358.1, 363.01, 453.1, 454.11, 455.11, 250/492.1; 362/227, 241, 245, 246, 247, 362/296.01, 297; 356/236, 244, 445, 446; 359/599; 73/865.6

See application file for complete search history.

(56) References Cited

U.S. PATENT DOCUMENTS

| | | | |
|---|---|---|---|
| 3,872,349 A | 3/1975 | Spero et al. |
| 3,911,318 A | 10/1975 | Spero et al. |
| 4,042,850 A | 8/1977 | Ury et al. |
| 4,062,996 A | 12/1977 | Keafer, Jr. et al. |
| 4,313,969 A | 2/1982 | Matthews et al. |
| 4,583,860 A | 4/1986 | Butner |
| 4,839,522 A | 6/1989 | Bourgeois et al. |

(Continued)

OTHER PUBLICATIONS

Chin et al., "Integrating Sphere Sources for UV Exposure: A Novel Approach to the Artificial UV Weathering of Coatings, Plastics, and Composites", 2002, pp. 144-160, Methodology and Metrologies, American Chemical Society Symposium Series 805.

(Continued)

*Primary Examiner* — Bernard E Souw
(74) *Attorney, Agent, or Firm* — Fitch, Even, Tabin & Flannery, LLP

(57) ABSTRACT

Integrating optical systems and methods of use are described herein. In one embodiment, an integrating optical system comprises: a housing having a first and second portions; and a chamber having a diffuse reflective material and a volume formed within the portions when coupled together. The portions are separable to allow insertion and removal of at least one light treatable object in and out of the chamber. At least one aperture is formed in the chamber to couple to a light source and to direct light from the light source to at least a first portion of the diffuse reflective material. At least one holding structure supports the object within the volume at a location, wherein the diffuse reflective material, the aperture and the location ensure that the light is diffusely reflected to integrate the light and impact the object with substantially uniform light without movement of the object.

27 Claims, 22 Drawing Sheets

U.S. PATENT DOCUMENTS

| | | | |
|---|---|---|---|
| 4,880,677 A | | 11/1989 | Hecq et al. |
| 4,907,887 A | * | 3/1990 | Leonard et al. ............... 356/519 |
| 5,251,004 A | | 10/1993 | Doiron et al. |
| 5,497,004 A | | 3/1996 | Rudolph et al. |
| 5,517,315 A | | 5/1996 | Snail et al. |
| 5,689,364 A | | 11/1997 | McGregor et al. |
| 5,745,234 A | | 4/1998 | Snail et al. |
| 5,781,342 A | | 7/1998 | Hannon et al. |
| 5,903,091 A | | 5/1999 | MacLennan et al. |
| 6,005,249 A | | 12/1999 | Hayes, Jr. et al. |
| 6,166,389 A | | 12/2000 | Shie et al. |
| 6,222,623 B1 | * | 4/2001 | Wetherell ...................... 356/236 |
| 6,226,085 B1 | * | 5/2001 | Weber .......................... 356/600 |
| 6,229,328 B1 | | 5/2001 | Lueders |
| 6,424,413 B1 | * | 7/2002 | Weber et al. .................. 356/236 |
| 6,583,879 B1 | | 6/2003 | Berg et al. |
| 6,626,052 B1 | | 9/2003 | Martin et al. |
| 6,866,899 B2 | | 3/2005 | Wright |
| 7,248,350 B2 | | 7/2007 | Kettler |
| 7,401,943 B2 | | 7/2008 | Okamitsu et al. |
| 7,508,503 B2 | | 3/2009 | Jang |
| 7,532,324 B2 | * | 5/2009 | Liu et al. ....................... 356/326 |
| 2005/0023478 A1 | | 2/2005 | Ruckman et al. |
| 2005/0115498 A1 | * | 6/2005 | Ingram et al. ................. 118/642 |
| 2008/0013082 A1 | | 1/2008 | Cutlip |
| 2008/0129996 A1 | * | 6/2008 | Liu et al. ....................... 356/326 |
| 2008/0262117 A1 | | 10/2008 | Avakian et al. |
| 2008/0285276 A1 | | 11/2008 | Okamitsu et al. |
| 2011/0108741 A1 | * | 5/2011 | Ingram ...................... 250/492.1 |

OTHER PUBLICATIONS

Gigahertz-Optik, "Diffuse Reflectors", published at least on or before Dec. 16, 2009, pp. 123-130, Gigahertz-Optik, Germany.

Hoffman Sphereoptics, "Integrating Sphere Design and Applications, Technical Information," 2004, pp. 1-20, Hoffman SphereOptics, Concord, NH.

Labsphere, "A Guide to Integrating Sphere Radiometry and Photometry, Tech Guide," published at least on or before Nov. 12, 2009, pp. 1-25, Labsphere Inc., North Sutton, NH.

Labsphere, "A Guide to Integrating Sphere Theory and Applications, Tech Guide," published at least on or before Nov. 12, 2009, pp. 1-19, Labsphere Inc., North Sutton, NH.

Labsphere, "Optical-Grade Spectralon Material," published at least on or before Nov. 12, 2009, pp. 1-2, Labsphere Inc., North Sutton, NH.

Optronic Laboratories, "Optolon 2: The Integrating Sphere Coating of the Future," published at least on or before Nov. 12, 2009, pp. 1-3, Optronic Laboratories, Orlando, FL.

Pike Technologies, "Integrating Spheres—Introduction and Theory," 2005, pp. 1-2, Pike Technologies, Madison, WI.

Saunders et al., "Roughened Quartz Surfaces and Teflon as small angle diffusers and depolarizers between 200 and 400 nm," Aug. 1, 1989, pp. 3242-3245, Applied Optics, vol. 28, No. 15, Gaithersburg, MD.

The Dow Chemical Company, Chin et al., "Ultraviolet Chambers based on Integrating Spheres for Use in Artificial Weathering," Nov. 5, 2001, pp. 1-17, The Proceedings of the $70^{th}$ Annual Meeting, Technical Program of the FSCT, Atlanta, Georgia.

W.L. Gore & Associates, Inc., "Gore DRP Diffuse Reflector Material," published at least on or before Mar. 2010, pp. 1-11, W.L. Gore & Associates, Inc., Newark, DE.

EXFO, "Catheter Assembly," Sep. 7, 2010, p. 1, published at http://www.exfo-omnicure.com/applications-catheter-assembly.php?tab=1.

JH Technologies, "EXFO Cure Ring," Sep. 8, 2010, pp. 1-2, published at http://www.jhtechnologies.com/uvcuring/opter.shtml.

EXFO, "OmniCure Assembly Solutions: Ablation Catheters," Oct. 16, 2009, pp. 1-5, published on Oct. 16, 2009, EXFO, Mississauga, Ontario, Canada.

EXFO, "OmniCure Assembly Solutions: Bonding of Balloon Catheters," Aug. 4, 2009, pp. 1-5, published on Aug. 4, 2009, EXFO, Mississauga, Ontario, Canada.

EXFO, "OmniCure: Setting the Standard for Precision UV Bonding," pp. 1-12, published at least on or before Sep. 8, 2010, EXFO, Mississauga, Ontario, Canada.

EXFO, "OmniCure Cure Ring Radiometer," Sep. 8, 2010, pp. 1-2, published at http://www.exfo-omnicure.com/products-cure-ring.php.

EXFO, "Cure Ring," Sep. 8, 2010, pp. 1-3, published at http://www.exfo-omnicure.com/products-cure-ring-a.php.

Keithley Instruments, Inc., "Measuring Laser Diode Optical Power With the Keithley Model 2500INT Integrating Sphere," published at least on or before Aug. 16, 2010, pp. 1-4, Keithley Instruments, Inc., Cleveland, OH.

DYMAX, "Guide to Selecting and Using DYMAX UV Light Curing Systems," published at least on or before Sep. 7, 2010, pp. 1-20, DYMAX, Torrington, CT.

DYMAX, "Complete UV Light Curing Flood Systems," published at least on or before Sep. 7, 2010, pp. 1-2, DYMAX, Torrington, CT.

DYMAX, "2000-EC and 5000-EC UV Light Curing Flood Systems," published at least on or before Sep. 7, 2010, pp. 1-4, DYMAX, Torrington, CT.

* cited by examiner

INTEGRATING OPTICAL SYSTEMS AND METHODS

This application claims the benefit of U.S. Provisional Application No. 61/381,165, filed Sep. 9, 2010, which is incorporated in its entirety herein by reference.

BACKGROUND OF THE INVENTION

1. Field of the Invention

The present invention relates generally to optical systems and methods. More particularly, the present invention relates to integrating optical systems and methods.

2. Disclosure of the Related Art

Many devices are assembled using a UV activated adhesive. When UV light of the proper wavelengths and incidence (power per unit area) impinges on the adhesive at the bond line for the proper length of time, the adhesive will harden. The required wavelength band, incidence and time of exposure vary according to the formulation of the particular adhesive used. The time of exposure, in combination with UV incidence, determines the dose (energy per unit area) applied to the object. The required wavelengths are generally polychromatic (broad band), as produced by an arc lamp for example; however, narrow band radiation, as produced by an LED or laser, is sometimes used.

In a typical UV curing application, the required UV incidence on the part can range from a few $mW/cm^2$ to several $W/cm^2$, for example, between 100 $mW/cm^2$ and a 1500 $mW/cm^2$. Generally, incidence is understood as the irradiance incident on a surface. Required wavelengths range from 200 nm to 600 nm, for example, wavelengths between 250 nm and 450 nm are used. Most commonly, wavelengths between 300 nm and 400 nm are used.

Assembled devices generally have a UV cured surface or adhesive extending over complex surfaces. For example, for medical applications, balloons may be glued to catheters used in angioplasty procedures. The balloon is slid over the end of the catheter; glue is applied to the balloon/catheter interface such that the entire cylindrical interface is wetted. This cylindrical surface must then be cured.

Surfaces other than cylindrical are also common, such as bonding a Y- or T-connector to IV (intravenous) tubing. Oftentimes the bond line at the connector/IV tubing interface must be cured by transmitting light thru one of or more of the objects being assembled, as part of the bond line lies on the side of the object opposite the light source.

Some objects require more than one bond line. Catheter balloons, for example, may require a bond at both ends of the balloon, and the bond lines may be separated by one or more centimeters. Several radiomarkers may be assembled on a single catheter, separated by several centimeters. An inline Y- or T-connection in an IV line will have 3 or 4 different cylindrical bond regions.

Commonly, the light sources used for curing these devices are "spot cure" systems. These systems consist of a small arc lamp, a reflector and a light guide. The arc is focused by the reflector onto the input surface of the light guide. Light is coupled into the light guide and transmitted to the output end. The output radiation pattern from the light guide is a circular "spot" projected onto a plane; the diameter of the spot increases with distance away from the light guide.

The light guide may be furcated. This divides the input optical power among the furcations. These branches are then located around the object to provide irradiation of the object from different directions in an effort to improve uniformity. Each branch produces a spot of light, just as the non-furcated light guide. Furthermore, the irradiance from each branch is 1/n of the non-furcated light guide output, where "n" is the number of furcations. This reduces the irradiance on the object by 1/n in order to improve uniformity. A typical light guide is either liquid filled or quartz fiber bundles.

During curing, the object temperature will increase with increasing optical energy absorbed by the irradiated components. Because the devices being cured are usually small and thin, the absorbed energy must be minimized to prevent thermal damage to the exposed components. Thus is it is very important to minimize the UV incidence and dose while meeting the requirements for curing the entire part. This is best achieved with uniformly applied UV light. A perfectly uniform light field will bring all areas to full cure at the same time, minimizing heat generated in the part.

Other known approaches involve UV flood curing systems in which UV light from the light source is spread over a large area, say 5 inches by 5 inches for example. However, the UV curing light is non-uniformly distributed over the treatment surface. That is, the UV curing light has the highest irradiance at the center of the treatment area and falls off moving toward the edge of the treatment area. Furthermore, the UV curing light is incident from only one direction (the location of the source) and so does not uniformly illuminate the side of the object that is away from the source. Known UV spot and flood light curing systems for curing medical components are available from many companies, such as Dymax Corporation of Torrington, Conn.

Another approach is known as a cure ring, for example, commercially available from Lumen Dynamics Group, Inc. (formerly Exfo, Inc.). A cure ring is an adapter that goes on the end of a light guide and converts the conical light guide output to an annular ring of inwardly directed light, much like a donut hanging by a thread, where the thread is the input light guide, the donut is the cure ring and the inner edge of the donut hole is the output light surface.

Some conventional systems attempt to maintain a constant exitance at the output of the light guide since the light source output deteriorates over time. For example, a detector measures the irradiance at a point near the input to the light guide. As the lamp output power degrades, the detected irradiance decreases as does the irradiance at the light guide input surface. The detected irradiance stays in fixed relation to the irradiance at the light guide input surface due to the system geometry. As the detected irradiance drops, a feedback control system causes the power coupled to the light guide input face to increase either by increasing the lamp power or by opening an aperture that otherwise reduces power coupled to the light guide.

What is needed is a system and related methods to reliably and repeatably treat objects with substantially uniform irradiation over multiple surfaces of the object while minimizing over-exposure of portions of the object. Preferably such systems should allow for easy object insertion and removal for treatment or curing.

SUMMARY OF THE INVENTION

Several embodiments provide integrating optical systems and methods of use. In one embodiment, an integrating optical system comprises: a housing having a first portion and a second portion, the first portion being coupled to the second portion; and a chamber having a volume and formed within the first portion and the second portion when coupled together, the chamber comprising a diffuse reflective material, wherein the first portion is separable from the second portion to allow insertion and removal of at least one light treatable object in and out of the chamber. At least one aperture is formed in the chamber and is configured to couple to a light source and is oriented to direct light from the light source to at least a first portion of the diffuse reflective material. At least one holding structure is coupled to the chamber and is configured to support the at least one light treatable object within the volume at a location, wherein the diffuse reflective material, the at least one aperture and the location ensure that the light from the light source is diffusely reflected by at least one portion of the diffuse reflective material to integrate the light within the volume and impact the at least one light treatable object with substantially uniform light without movement of the at least one light treatable object.

In another embodiment, a method of treating at least one treatable object, comprises the steps: providing light, through an aperture, within a chamber from at least one light source, wherein the chamber has a volume and is formed within a first portion and a second portion of a housing when the first portion and second portion are coupled together, wherein the first portion is separable from the second portion to allow insertion and removal of the at least one light treatable object in and out of the chamber, wherein the chamber further comprises a diffuse reflective material; and diffusely reflecting the light from at least a first portion of the diffuse reflective material so that the light from the at least one light source is integrated within the volume and impacts the at least one light treatable object being supported by at least one holding structure with substantially uniform light without movement of the light treatable object.

In a further embodiment, a method for use with an integrating optical device, comprises the steps: measuring an amount of diffusely reflected light at a surface within a chamber; establishing, based on the amount of the diffusely reflected light, a feedback parameter that is proportional to an irradiance of at least one light treatable object within the chamber, the diffusely reflected light being integrated within the chamber to provide the irradiance comprising substantially uniform light; and adjusting the irradiance in the chamber from at least one light source based on the feedback parameter.

In a further embodiment, an integrating optical system, comprises: a housing comprising a first portion and a second portion, the first portion being coupled to the second portion; a chamber having a volume and formed within the first portion and the second portion when coupled together, the chamber comprising a diffuse reflective material; at least one aperture formed in the chamber; a third portion of the housing; and at least one light source integrated within the third portion of the housing and configured such that light from the light source is focused at or near the aperture and a diameter of the aperture is no more than 5 times a diameter of a focal spot of the light. The light is oriented to impact at least a portion of the diffuse reflective material, and wherein the diffuse reflective material and the at least one aperture ensure that the light from the light source is diffusely reflected by at least one portion of the diffuse reflective material to integrate the light within the volume and impact a light treatable object located within the volume with substantially uniform light without movement of the light treatable object.

BRIEF DESCRIPTION OF THE DRAWINGS

The above and other aspects, features and advantages of several embodiments of the present invention will be more apparent from the following more particular description thereof, presented in conjunction with the following drawings.

DETAILED DESCRIPTION

Figure 1:
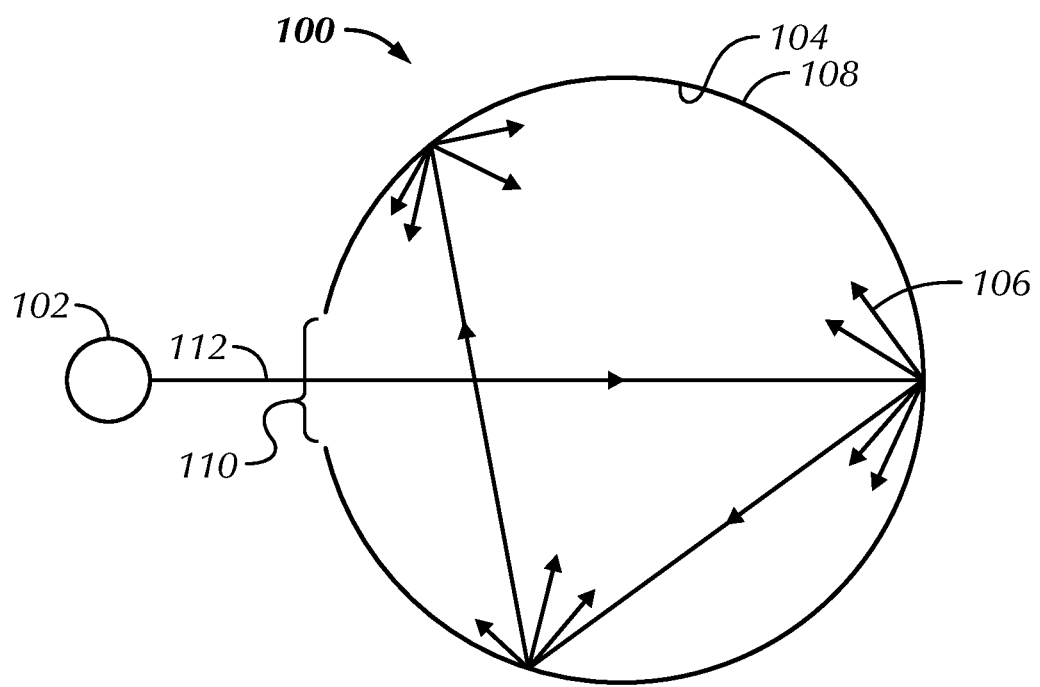
FIG. 1 is an exemplary schematic diagram illustrating a conventional integrating sphere system.

The following description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Problems with Known Light Treatment and Curing Approaches

There are several problems with known systems and methods of treating objects with light, for example, for curing objects with UV light. In some embodiments, UV light is used to cure UV activated adhesives used in assembling small medical devices, such as catheters, balloons, various joints, and so on.

When objects are cured directly from a light guide, the incidence is very non-uniform. Conventional methods irradiate the object directly with the light guide. The irradiance profile from the light guide is very non-uniform, causing non-uniform curing of the object. The non-uniformity may be improved somewhat with output optics (lenses) on the end of the light guides at significant additional cost.

Furthermore, some conventional curing methods have poor uniformity due to light source geometry and light absorption by the device. In the case of the balloon catheter, for example, the treated object is cylindrical. A single light guide will apply light from a single azimuth angle only. The light guide output will be extended over an area much larger than the object, wasting light. Furthermore, the radiation from the light guide will not be uniform on the bond line, since the angle of incidence on the bond line will vary along the line and since radiation is absorbed by the part. In particular, the bond line on the object directly opposite the light guide will be poorly irradiated and the irradiation profile along the bond line will be very non-uniform. In some cases, non-uniform UV dosage at the bond line can result in over and under-cured bond portions, and possible later bond failure. In implementations where the bond line is part of a medical device to be inserted into a person's body, loss of adhesion of parts of the medical device can be catastrophic.

Conventional methods often use furcated light guides to improve uniformity which can overcome some of the non-uniformity by irradiating the bond line from several angles. Generally light guides with two, three or four furcations are used. However, even with a furcated light guide, bond line uniformity is poor. Furthermore, the light guide exitance (exitance is the irradiance leaving a surface) drops in proportion to the number of furcations, since the constant input power is divided equally among the furcations. Furthermore, furcated light guides are expensive. For example, a simple non-furcated light guide sells for as low as $500. A bifurcated light guide of the same quality sells for more than $2000. A four-furcated light guide of the same quality sells for more than $5000.

Furthermore, furcated liquid light guides must be balanced daily (to assure equal optical power exiting each branch) for repeatable operation. Furcated light guides are not suitable for use on bond lines that are separated by more than a few millimeters due to the non-uniformity of light exiting the individual branches. Often a catheter will have objects adhered to it separated axially by a few centimeters. These are generally cured one object at a time since direct light guides cannot cure objects that are separated by more than a few millimeters.

The output of light guides can be affected by age, use and installation of the guide. In standard fixturing, the irradiance at the object may be reduced over time due to light guide degradation. Repeated bending will reduce the output as well.

Inadvertently decreasing the bend radius of a light guide attached to the fixture will reduce the irradiance on the part.

Conventional methods may require part rotation or motion to improve uniformity. Many assemblies require a partial curing process where the part is exposed for a time less than is required for full dose on the minimally irradiated areas; then the part is moved (or the light source is moved) to a position more favorably exposing the most under-exposed areas; the part is further cured until the required dose is achieved on all surfaces. This is done to avoid thermal damage to the part due to overexposure. Essentially, a more uniform exposure is achieved by moving the part and/or the light source. However, the resulting irradiation is not well controlled and the assembly quality is poorly controlled.

Conventional methods may overexpose the devices due to non-uniformity of irradiation. The bond line must be exposed to radiation at a minimum incidence for a certain time until the target dose is reached. To ensure complete cure along the bond line, the lowest incidence region determines the exposure time. Thus, in non-uniform exposure systems, the exposure time is extended and significant regions of the assembly are overexposed. Thus, non-uniform exposure results in a longer exposure time, increasing object heating.

Conventional methods limit access to the device for assembly. The device may be held in a fixture to assist assembly, dispensing of adhesive and curing. A small amount of UV light may be applied to "tack" the components in place prior to further handling. More commonly, the adhesive is cured in the same fixture used for assembly. Access to the part in the fixture for applying adhesive is limited due to the presence of the light guide. If the light guide tips are removed during adhesive application and replaced after application, the resulting irradiance distribution is not repeatable due to variations in light guide performance under repeated assembly/disassembly.

Known cure rings have limited applications and do not work well for objects that are not essentially cylindrically shaped. It can also be difficult to manipulate the object into place inside the "donut hole." Objects must be located exactly on axis for uniform irradiance. The bond line must align with the cure ring output aperture plane for uniform irradiance as well. Performance depends on the quality of the light guide/cure ring connection, leading to poor repeatability. Further, azmuthial distribution of light from the cure ring aperture is not uniform, leading to non-uniform curing. Due to the constricted nature of the cure ring, it is difficult and often impossible to dispense adhesive with the object assembled in the cure region of the ring. The cure ring is fragile due to the technology used to distribute the light from a conical source out an annular aperture. Only one object may be cured at a time.

Furthermore, even though some systems use feedback to maintain a constant exitance from the light guide by measuring the light at the input of the light guide and adjusting the light source over time as the light source degrades, this feedback is at the light source, not at the object to be treated. That is, this conventional feedback only corrects for changes in lamp output. There are many factors that may make the irradiance at the object vary over time; for example, bends in the light guide, light guide degradation, and object location relative to light guide output aperture are all common problems and will cause the irradiance at the object to vary. This variation will not be detected by any feedback control system that relies on light guide input irradiance. In any event, it is impractical, and in many cases impossible, to measure the true incidence on the part being cured. Usually, there simply is not enough room to place a radiometer in the location of the part to measure the irradiance during the cure.

Additionally, this known feedback method is not flexible in that different objects require different total dose to reach desired cure. Thus, this method is unable to control the irradiance or dose delivered to the object; it only controls the power input to the light guide. Dose is the time integral of irradiance on the object and it is the dose that determines the cure of the UV curable material. These known feedback control systems do not control the dose to the object.

DESCRIPTION OF EMBODIMENTS

One or more embodiments address one or more of the problems noted above, and/or other problems not specifically described, for example, resulting in higher quality light treatments in less time. In some embodiments, systems and methods are provided to treat objects with a light treatment. In some embodiments, the systems and methods are provided to treat small, heat sensitive objects being assembled with uniform UV radiation at the proper incidence and wavelength band. In some embodiments, light treatment is not limited to UV radiation, e.g., in some embodiments, light treatments may comprise UV, visible and/or infrared (IR) light. That is, in some embodiments, the light treatment comprises light having at least a portion of the spectral range of less than 180 nm to up to 3000 nm and beyond. In some embodiments, the light treatment is for curing (e.g., UV, IR or thermal curing) an object and/or sterilization of at least one surface of the object. In some embodiments, the system also serves as a fixture for the assembly and wetting of the parts, controlling the applied irradiance and dose and/or eliminating the use of light guides. In some embodiments, reliable and highly repeatable systems and methods are provided to treat objects with substantially uniform irradiation over multiple surfaces of the object while not over-exposing portions of the object. In some embodiments, the systems and methods do not require rotation or movement of the object being treated during treatment. In some embodiments, the systems and methods allow for easy object insertion and removal for treatment or curing. In some embodiments, a dose control system is provided that measures the exitance of a chamber wall, which is proportional to the irradiance at the object, which is used to measure the dose of light received at the object itself. In one form of such embodiments, it is possible to maintain a substantially constant irradiance at the object while controlling the total dose delivered to the object. In some embodiments, the systems and methods are light curing systems for curing coatings and adhesives on small devices, especially small medical devices, to adhere such things as balloons, radiomarkers, electrodes and other objects to catheters, guidewires and cannulas; coating and curing molded hearing aids; adhering objects to IV (intravenous) tubing; adhering needles to hubs and syringes. In some embodiments, the systems and methods use an optical integrating system architecture, for example, an integrating sphere architecture. Further details are provided below of these and other embodiments.

Conventional integrating optical systems, such as integrating spheres, are typically used for characterizing the surface properties of materials by making a variety of optical, photometric, and radiometric measurements. Integrating spheres are optical apparati typically comprising a hollow spherical cavity with its interior having a high diffuse reflectivity for providing a largely uniform scattering or diffusing effect. The spheres typically have entrance and exit ports. Light rays incident on any point on the inner surface are, by multiple scattering reflections, uniformly distributed to all other such points, thereby minimizing the effect of the light's original direction. An integrating sphere preserves power, but destroys spatial information. It is typically used with a light source and a detector for making optical power measurements. An example of a typical integrating sphere architecture is explained as follows.

Referring to FIG. 1, an exemplary schematic diagram illustrating a conventional integrating sphere system 100 is shown which comprises a housing 108 having an input port 110, a light source 102 disposed outside the housing 108 and diffuse reflective material 104 disposed on the interior surface of the housing 108. A first incidence of light 112 originating from the light source 102 is diffusely reflected from the far surface of the housing 108 so as to create diffusely reflected light 106, wherein the diffusely reflected light 106 is diffusely reflected from various surfaces of the housing 108 until substantially uniform light is achieved throughout the sphere.

Figure 2:
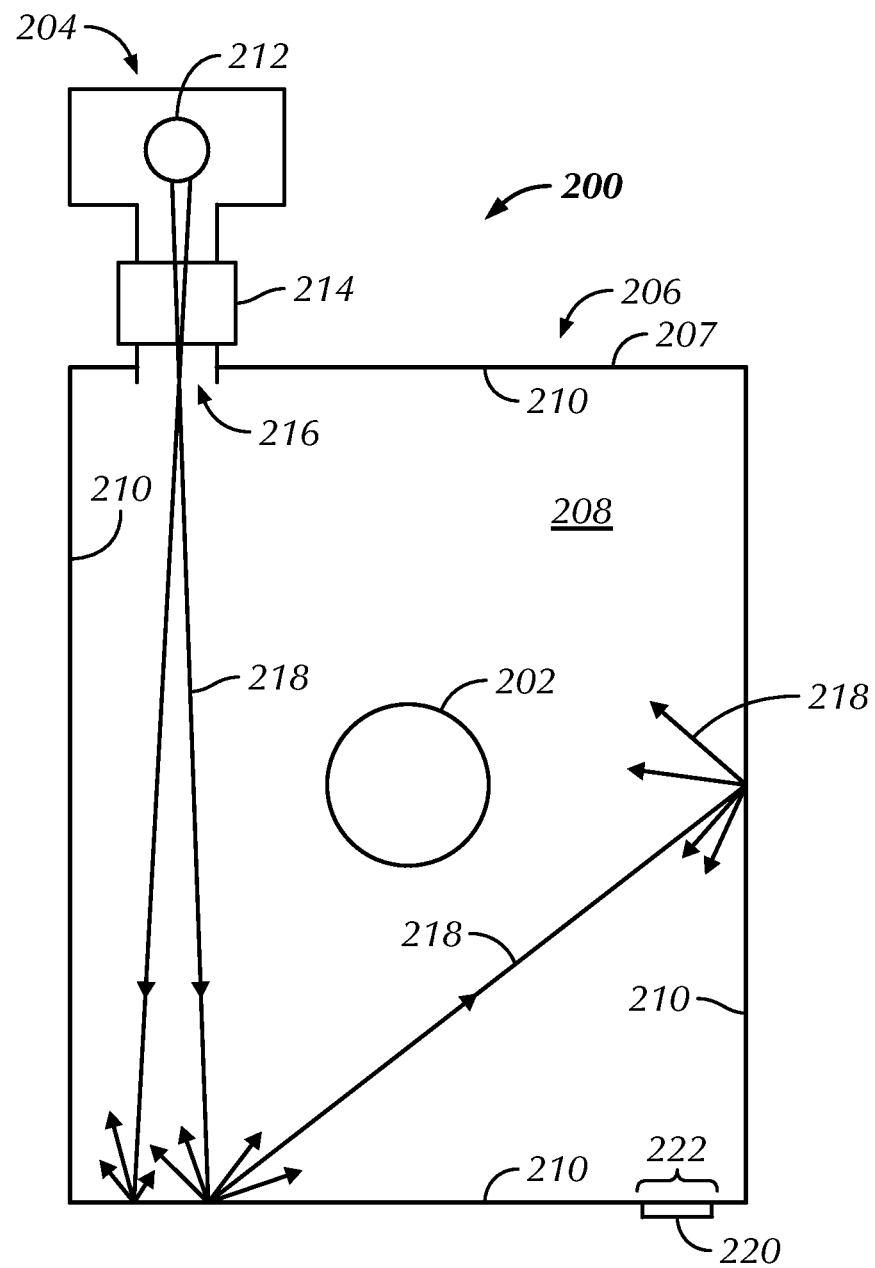
FIG. 2 is a schematic diagram illustrating an integrating optical system for treating an object in which a light source assembly is coupled to an integrating optical chamber in accordance with several embodiments.

Referring next to FIG. 2, shown is a schematic diagram illustrating an integrating optical system 200 for treating an object 202 in which a light source assembly 204 is coupled to an integrating optical chamber 206 in accordance with several embodiments. In this embodiment, the integrating optical chamber 206 (also referred to as chamber 206) comprises a housing 207 having an interior that forms a volume 208 within which the object 202 is located. At least a portion of an interior surface of the housing 207 includes a diffuse reflective material 210. In some embodiments, the diffuse reflective material surrounds the object 202. The light source assembly 204 includes a light source 212, one or more light power source, reflectors, optics, filters, and/or other known components (not shown). A light guide 214 couples light from the light source to the chamber via an aperture 216. Typical light guides comprising fiber optic bundles or a light conducting liquid filled conduit. In this way, the light source assembly and the chamber are not integrated with each other. That is, they may be separately manufactured and coupled together using the light guide 214.

In operation, the object is inserted into the volume to be treated with light from the light source, e.g., cured with UV light from a UV light source, or at least one surface of the object is substantially sterilized. Depending on the embodiment, the light source may be one or more of a UV, visible and/or IR light source. Thus, in some embodiments, the light source 212 is one or more light sources that provide light having at least a portion of the spectral range of less than 180 nm to up to 3000 nm and beyond. In some embodiments, the light treatment is a narrowband source or a broadband source. In some embodiments, the light source may be one or more lamps, diodes or lasers. Example light treatments include curing, artificially weathering, disinfecting, and the like. Once the object is within the volume, the light source is activated and light rays are coupled into the chamber via the light guide 214 and the aperture 216. The light guide and aperture are located and configured to direct the entering rays to first impact an interior surface of the chamber and be diffusely reflected by the diffuse reflective material 210. The entering light rays are typically reflected multiple times within the volume before being incident on the object 202. In some embodiments, there are no light rays that directly impact the object without first being diffusely reflected. Thus, according to known integrating sphere functionality, the diffusely reflected light is integrated within the volume to form a substantially uniform irradiance of light incident on the object. Having been illuminated with substantially uniform light at certain wavelength/s and for a certain time or dose, the object is treated (e.g., cured) and the light treatment is stopped and the object is removed from the chamber. Although the light rays 218 entering the volume 208 are shown as diverging, in other embodiments, depending on the light guide 214 characteristics, the entering light rays may be diverging, collimated or converging.

Figure 29:
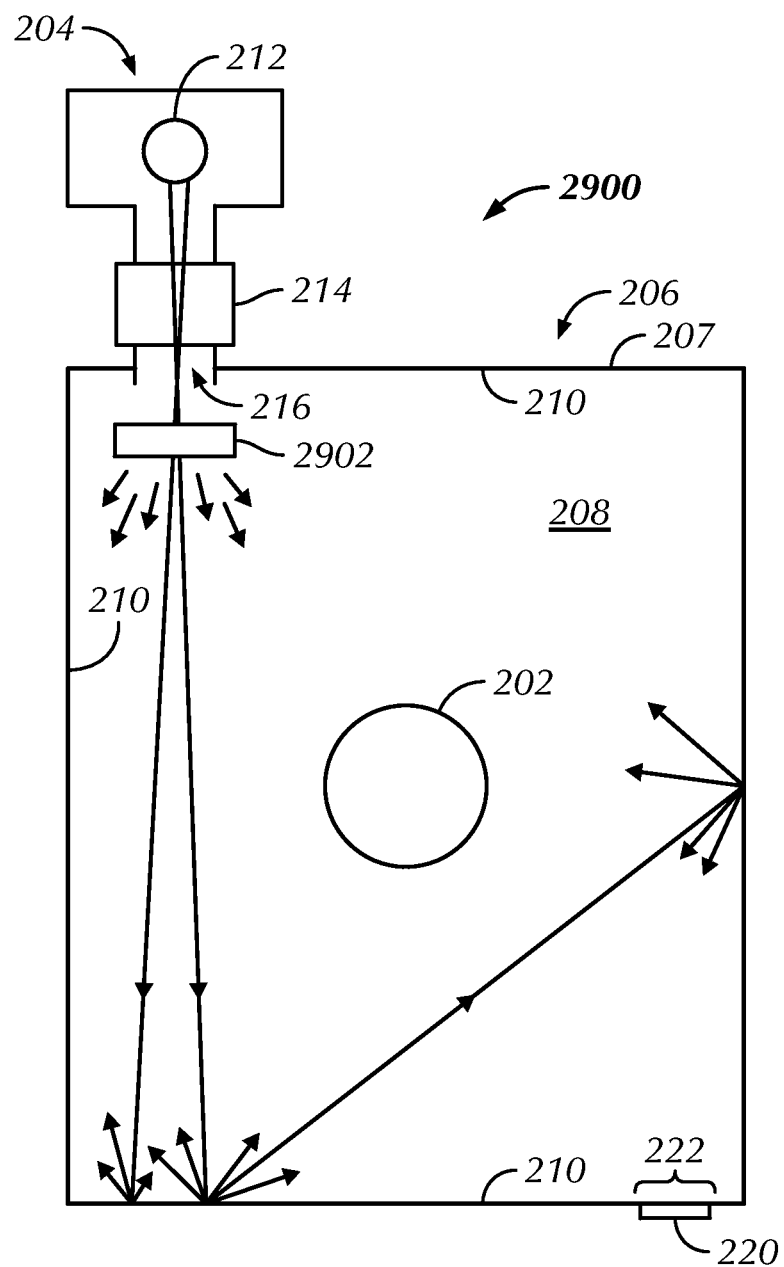
FIG. 29 is a schematic diagram illustrating an integrating optical system for treating an object in which a light source assembly is coupled to an integrating optical chamber including a diffuse transmissive baffle in accordance with several embodiments.

In some embodiments, a diffuse transmissive baffle 2902 (see the system 2900 of FIG. 29) may be located at the aperture or within the volume 208 (as illustrated in FIG. 29). This baffle 2902 is positioned between a location of the object 202 and the aperture 216 in order to diffusely transmit and spread the entering light rays into the volume. The use of such a diffuse transmissive baffle 2902 may be helpful in some embodiments to reduce interior volume 208 of the chamber 206 while still achieving substantially the same level of uniformity of irradiation of the object 202. Additional details and description of various embodiments of a diffuse transmissive baffle can be found in U.S. application Ser. No. 12/639,407, filed Dec. 16, 2009, which is incorporated herein by reference. Although not illustrated, it should be possible to locate the object more directly under the baffle 2902. The other components of the system 2900 of FIG. 29 in common with the system 200 of FIG. 2 have the same functionality and discussion is thus not repeated for FIG. 29.

In this and other embodiments, the chamber 206 is shown having a rectanguloid configuration by example only, but may have any suitable configuration for accommodating the object. For example, in some embodiments, the chamber 206 comprises any suitable configuration, such as a sphere, a rectanguloid, a cube, a polyhedron, an ellipsoid, an ogivoid, a paraboloid, a cylinder, a hyperboloid of one sheet, a hyperboloid of two sheets, a hyperbolic paraboloid, and an elliptical cone, for accommodating the object.

In some embodiments, the diffuse reflective material 210 comprises a diffuse reflective material, such as, and not limited to, a diffuse reflective polymer, a conformal diffuse reflective polymer, a fluoropolymer, a perfluoroalkoxy, a fluoroethylene-propylene, a tetrafluoroethylene, an ethylene-tetrafluoroethylene, a polytetrafluoroethylene, a flexible polytetrafluoroethylene, an expanded polytetrafluoroethylene, a sintered polytetrafluoroethylene, a pressed polytetrafluoroethylene, and a barium sulfate. In some embodiments, this material may be positioned and/or adhered to interior surfaces of the chamber. In some embodiments, the diffuse reflective material comprises flexible, adhesive backed sheets of material, such as selected from the materials listed above or other material having diffuse reflective properties. In some embodiments, diffuse reflective material covers as much of the interior surfaces of the chamber as possible in order to minimize areas that are light absorbing or not diffusely reflecting.

In some embodiments, the target 202 comprises a material that is responsive to ultraviolet light, such as an ultraviolet-curable polymeric material, a radiation-curable material, a free-radical-polymerizable material, a disinfectable material, a weatherable material, and an artificially weatherable material, for example. Depending on the light treatments used, the target 202 may comprise a material that is responsive to the spectral properties of the light treatment used. For example, the target 202 comprises a material that is responsive to one or more of UV, visible and IR light.

The light source 212 may comprise a lighting element, such as a discharge lamp, a microwave-excited arc lamp, an electrodeless arc lamp, a low pressure arc lamp, a medium pressure arc lamp, a high pressure arc lamp, an incandescent lamp, one or more of an infrared, UV or visible light source, a light emitting diode, and a laser, for example. Optionally, in some embodiments, a quartz window, spectral filter or other transmissive structure or shutter may be positioned at the aperture 216 and/or within the light guide 214.

In some embodiments, various holding structures, such as those described herein for example, may be implemented to hold and locate the object 202 at a location in the volume to ensure substantially uniform irradiation and minimize any direct light rays from the aperture from impacting the object. For example, various shelves, tables, suspended wires, rods, bushing, mats may be used to hold and locate the object at a given location within the volume 208. Alternatively, if it is not necessarily to treat all portions (e.g., an underside) of an object, the object may be rested on a floor of the chamber.

In some embodiments, such as described more fully in this specification, a light sensor 220 may be implemented at a second aperture 222 of the chamber. In some embodiments, the sensor may detect light transmitted through the diffuse reflective material (e.g., the sensor is positioned behind the diffuse reflective material at an aperture in the chamber wall that is covered by the diffuse reflective material) rather than be coupled to an opening in diffuse reflective material, and in such embodiments a second aperture in the diffuse reflective material is not needed and losses due to such second aperture are avoided. In some embodiments, this light sensor is positioned such that its field of view does not include any light rays that have not been diffusely reflected within the chamber at least once. In some embodiments, the sensor 220 is a photodiode sensor that produces an output proportional to the power incident on the diode. Since the sensor field of view is fixed, the output is proportional to the exitance from the chamber wall. The object being cured is not in the field of view of the sensor. However, due to the integrating nature of the chamber (by design), the incidence on the object is proportional to the wall exitance. Therefore, the sensor output is proportional to the radiation incident on the object. In embodiments where the sensor is behind the diffuse reflective material, the sensor may be placed in multiple locations since the field of view of the sensor is the back side of the material 210, not into the volume 208.

By implementing a light treatment system and method using an integrating sphere architecture as variously configured according to one or more embodiments, one or more of the problems associated with known curing solutions are addressed. For example, substantially all surfaces of the object at multiple incident points and planes about all locations of the object are treated with substantially uniform light without over-exposing portions of the object. In some embodiments, this is accomplished without requiring the exact axial positioning of the object relative to the light guide and/or without having to rotate or move the object to be treated during treatment. Thus, some embodiments provide for effective treatment, e.g., curing, of small heat sensitive objects being assembled with uniform UV radiation at the proper incidence and wavelength band. In some embodiments, the system 200 is well suited for UV curing systems for curing coatings and adhesives on small devices, especially small medical devices, to adhere such things as balloons, radiomarkers, electrodes and other objects to catheters, guidewires and cannulas; coating and curing molded hearing aids; adhering objects to IV (intravenous) tubing; adhering needles to hubs and syringes. For example, since the light is uniform from substantially all directions, bond lines can be uniformly cured. It is understood that while many of the embodiments described herein specifically refer to the use of UV light, many embodiments use light sources providing light of other wavelengths, such as visible and/or IR, for example.

While more details of several embodiments follow this description, it is understood that any of the details and variations described in connection with the system 200 may be applied to one or more of the other embodiments described herein. Additionally, it is understood that features described throughout the rest of this specification may also be implemented in the system 200 or other systems and methods described herein.

Figure 3:
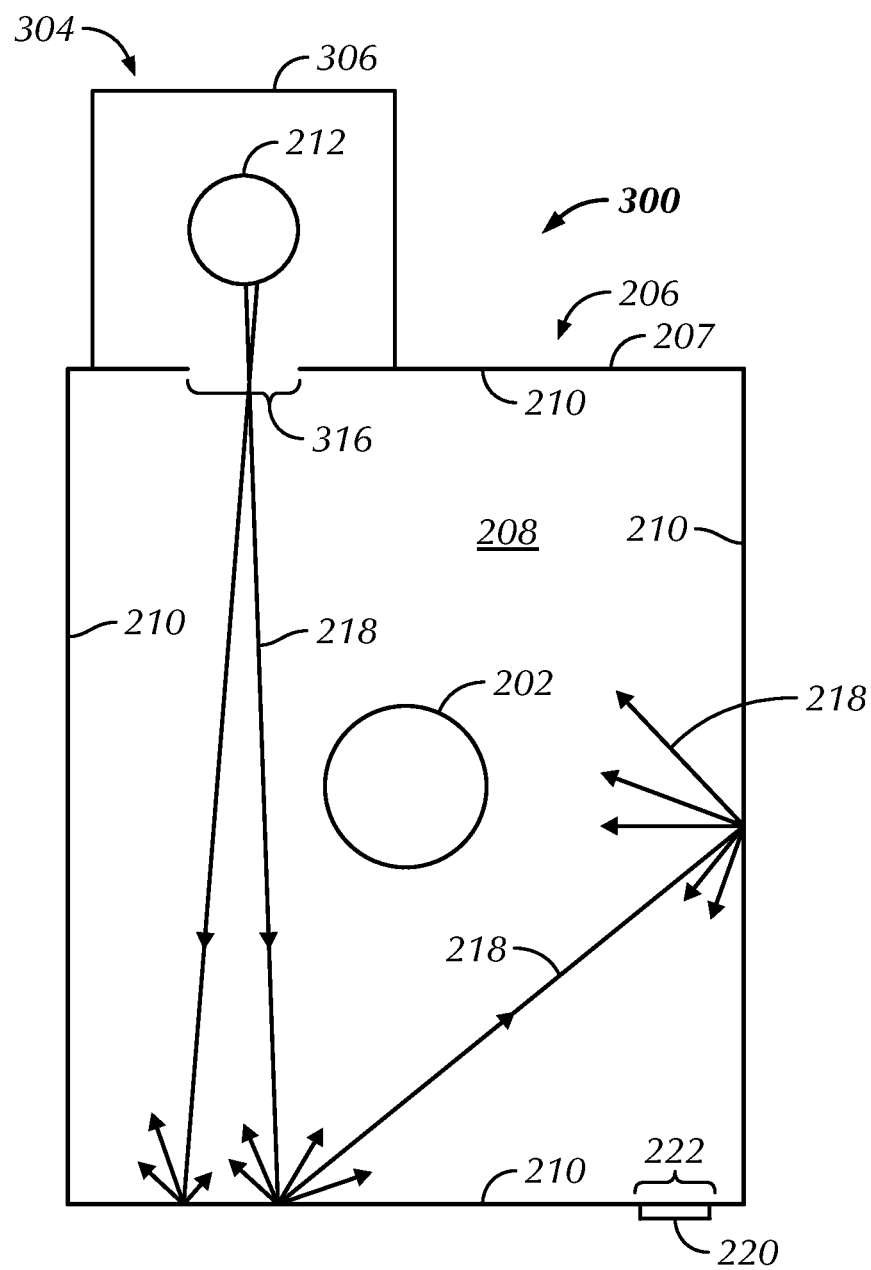
FIG. 3 is a schematic diagram illustrating an integrating optical system for treating an object in which a light source assembly is integrated with the integrating optical chamber in accordance with several embodiments.
Figure 30:
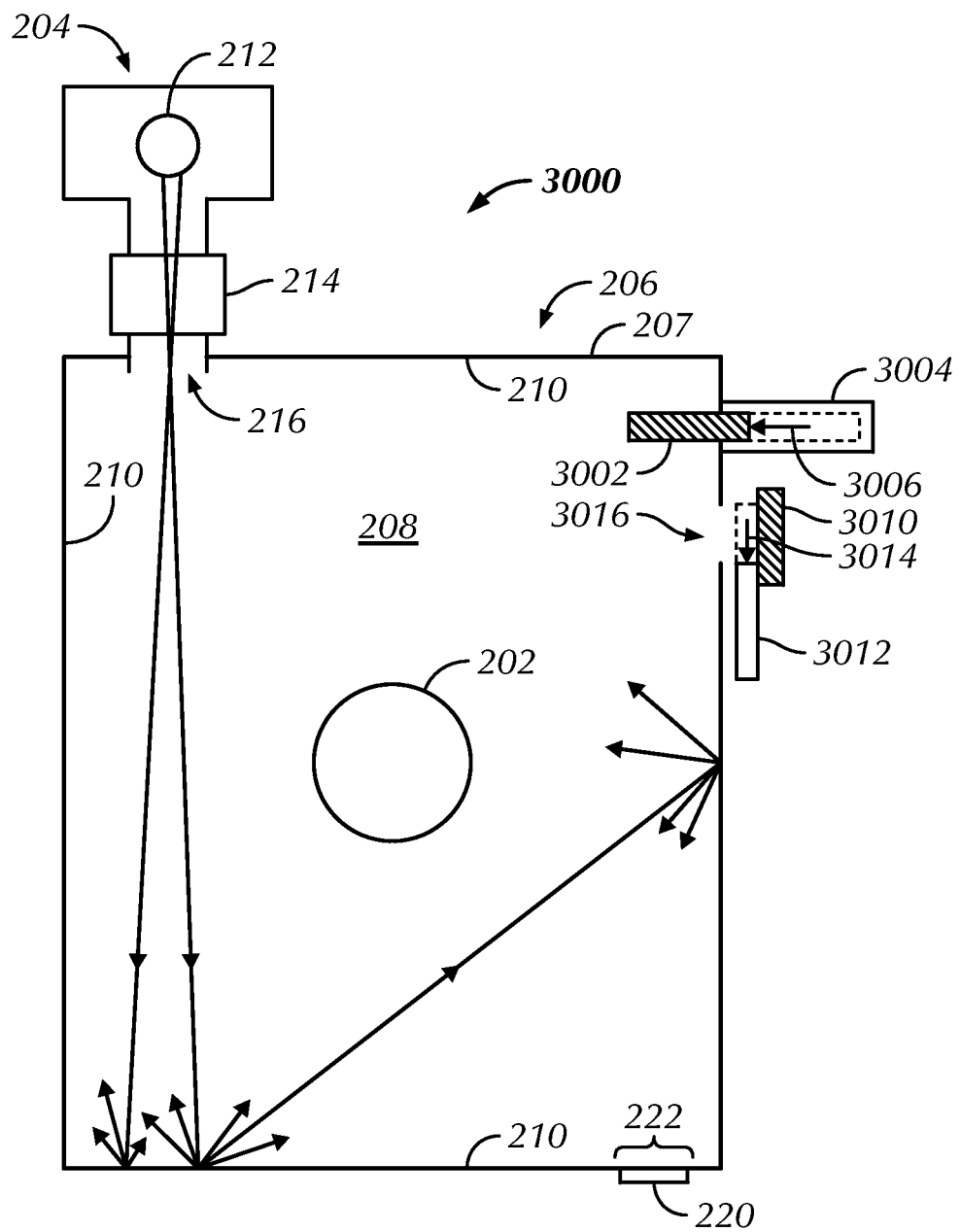
FIG. 30 is a schematic diagram illustrating an integrating optical system for treating an object in which a light source assembly is coupled to an integrating optical chamber including an element selectively moveable into the chamber and a selectable loss area opening created to adjust chamber irradiance in accordance with several embodiments Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

Referring next to FIG. 3, shown is a schematic diagram illustrating an integrating optical system 300 for treating an object 202 in which a light source assembly 304 is integrated with the integrating optical chamber 206 in accordance with several embodiments. Relative to the embodiment of FIG. 2, the light source assembly 304 includes a housing 306 and is configured to direct light rays into the chamber 206 via aperture 316. The light source assembly 304 includes the light source 212 and one or more one or more of a light power source, reflectors, optics, shutter, filters, and/or other known components (not shown). Additionally, a transmissive, filtering or quartz window may be positioned at the aperture 316. In some embodiments, the light source assembly 304 is configured to focus light from the light source at a focal plane at or near the plane of the aperture 316. For example, this allows the aperture to be small or minimized to reduce the non-diffusely reflecting portions of the volume 208. Further details of some embodiments are described in connection with FIG. 27. In operation, the system 300 operates similarly to the system 200 and may be variously embodied as the system 200. In the system 300, the entire system 300 is typically designed and manufactured by one manufacturer, whereas in the system 200, the optical integrating chamber 206 may be separately designed by different manufacturers than of the light guide 214 and the light source assembly 204. Similar to that described relative to FIG. 2, the system 300 of FIG. 3 may also incorporate use of a diffuse transmissive baffle 2902 (such as illustrated in FIG. 29) at the aperture or within the volume 208, or incorporate one or more elements 3002, 3010 or selectable loss area openings 3016 (such as illustrated in FIG. 30). This baffle 2902 would be positioned between a location of the object 202 and the aperture 316 in order to diffusely transmit and spread the entering light rays into the volume. The use of such a diffuse transmissive baffle 2902 may be helpful in some embodiments to reduce interior volume 208 of the chamber 206 while still achieving substantially the same level of uniformity of irradiation of the object 202. Additional details and description of various embodiments of a diffuse transmissive baffle can be found in U.S. application Ser. No. 12/639,407, filed Dec. 16, 2009, which is incorporated herein by reference. Although not illustrated, it should be possible to locate the object more directly under the baffle 2902.

Referring next to FIGS. 4-15B, several views are shown of an integrating optical system 400 comprising a housing including separable hinged portions in both open and closed configurations in accordance with several embodiments. Concurrent reference is made to one or more of FIGS. 4-15B.

Figure 4:
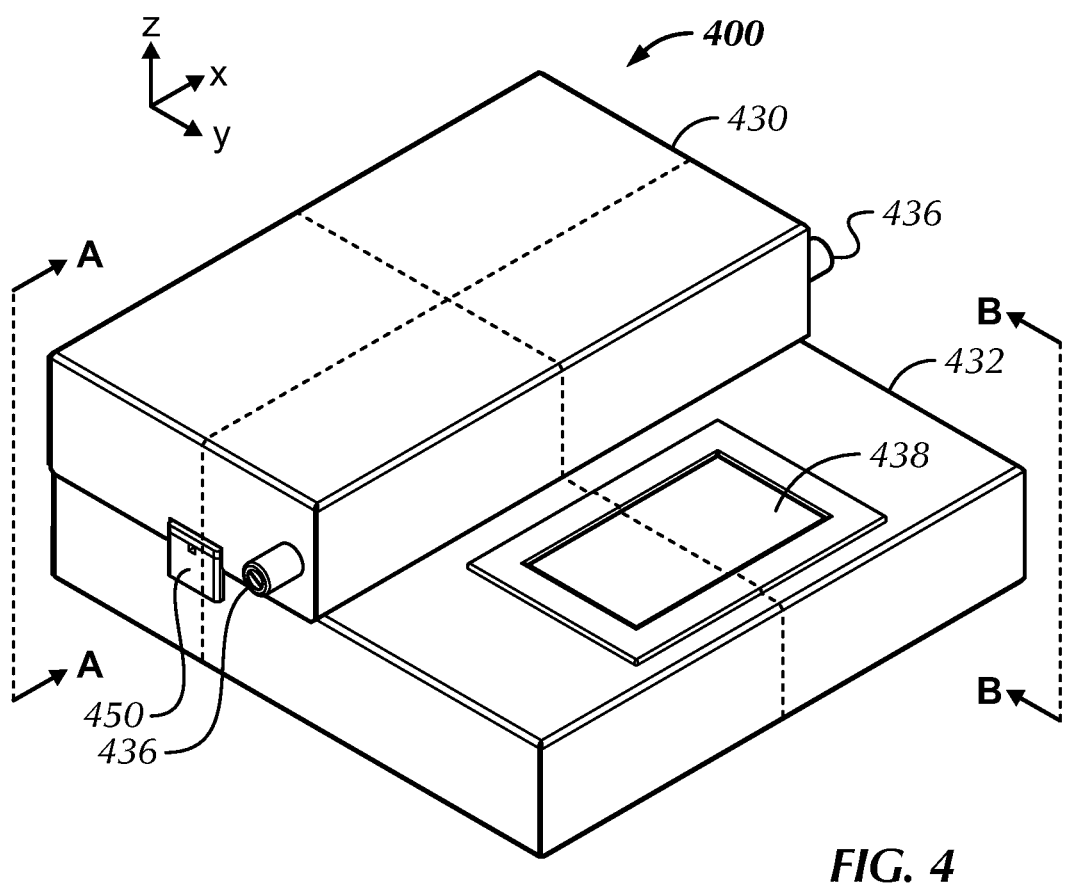
FIG. 4 is a front perspective view of an integrating optical system comprising a housing including separable hinged portions in a closed configuration in accordance with several embodiments.
Figure 5:
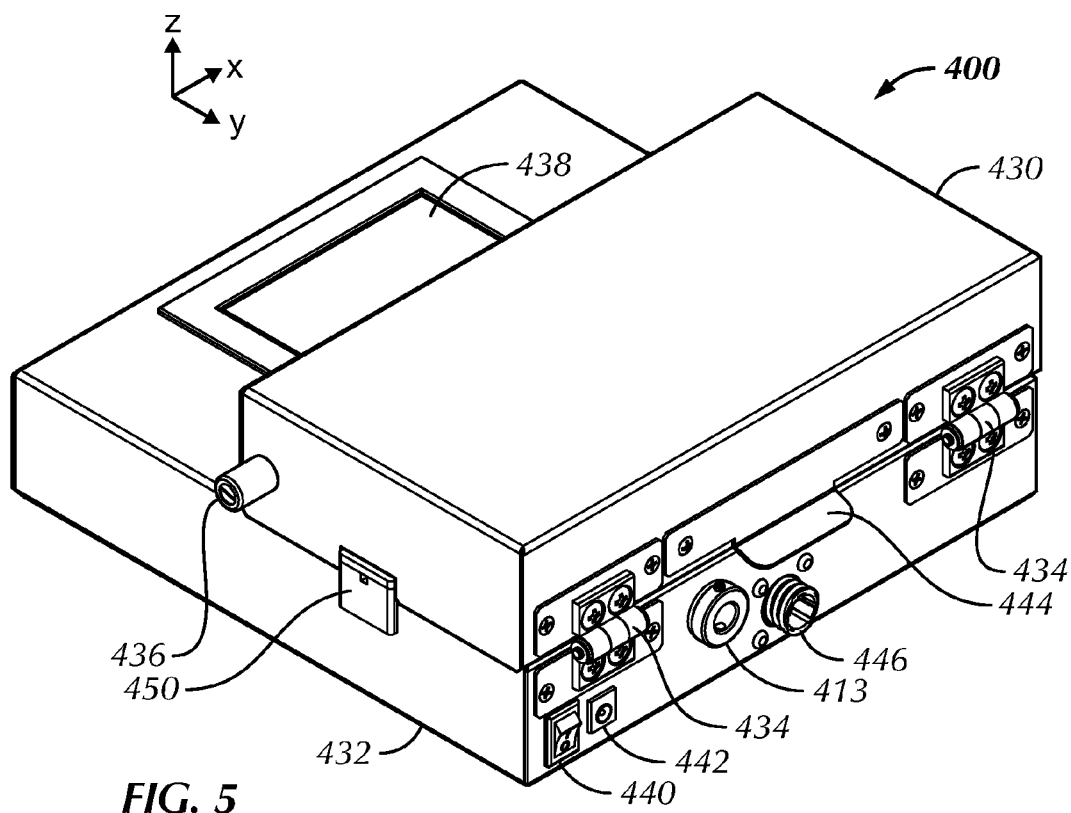
FIG. 5 is a rear perspective view of the integrating optical system of FIG. 4.
Figure 6:
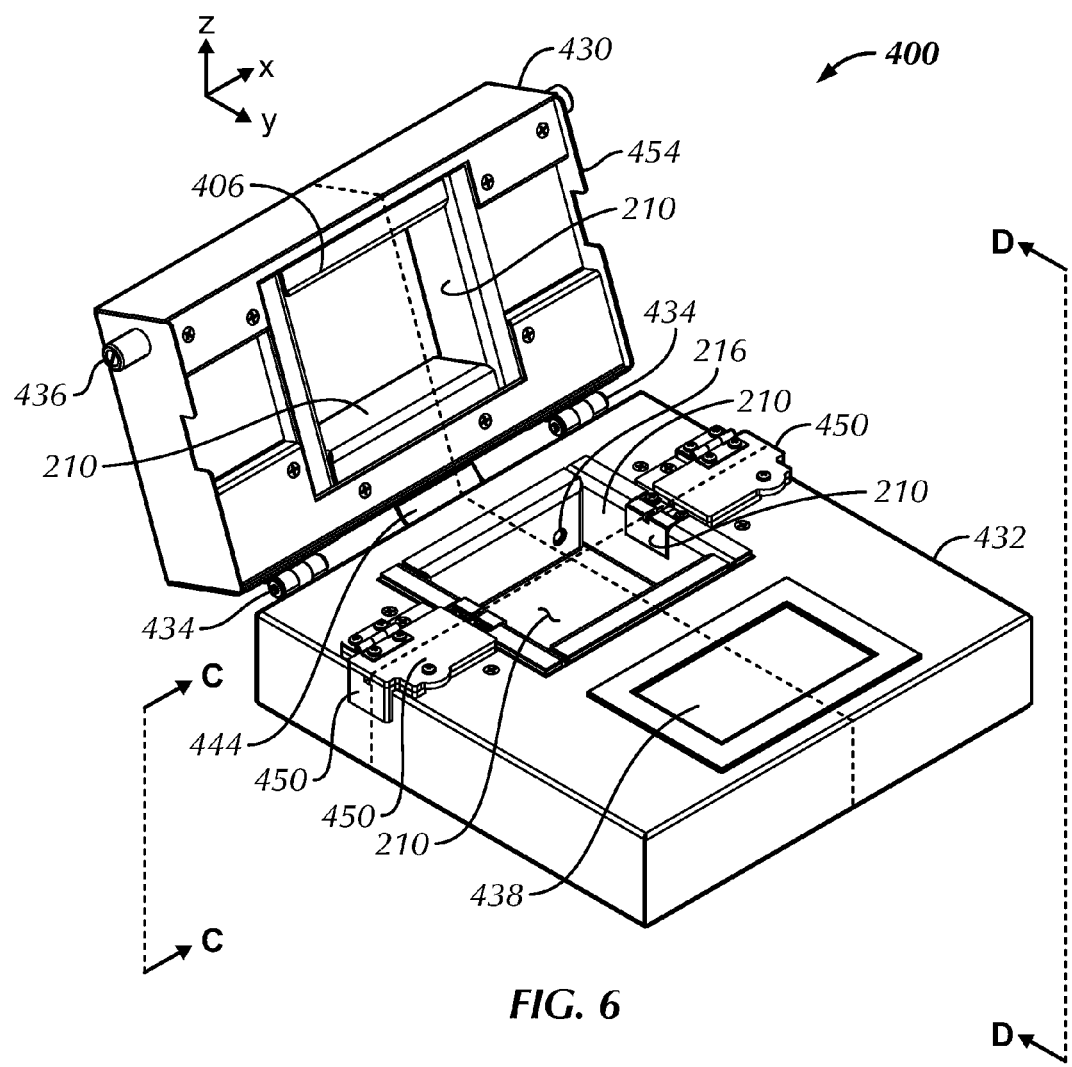
FIG. 6 is a front perspective view of the integrating optical system of FIG. 4 in which the separable portions are in an open configuration exposing portions of a volume of the integrating optical chamber in accordance with several embodiments.

FIG. 4 illustrates an integrating optical system 400 for treating an object (not shown) within an integrating optical chamber 406. A non-integrated light source assembly (not shown, similar to system 200 of FIG. 2) is coupled to the chamber 406 with a coupler 413 of a light guide 414 in accordance with several embodiments. A housing includes an upper portion 430 and a lower portion 432 that are hingably coupled together with hinges 434. Many types of hinges are suitable, such as butt (shown), continuous, friction, damper, spring and self closing, for example.

In the closed configuration (see FIGS. 4, 5, 7 and 9), the upper portion closes over, covers and is held in position (e.g., by weight, latch, springs, etc.) over the lower portion. In the closed configuration, a volume 408 within the optical integrating chamber is formed, a portion of the volume 408 formed within the upper portion and a portion of the volume formed within the lower portion. Handles 436 are used to lift and lower the upper portion relative to the lower portion. Also illustrated is a user interface comprising a touch sensitive display screen 438 and driving electronics 439. Also shown is a power switch 440, power input 442 (e.g., AC or DC power input connector), and input/output connector 446 to allow control connections and signals to a light source assembly (such as door interlock signals, door state signals, and "lamp on" signals to control the lamp or shutter state), for example. A limiter 444 including a tab is provided to limit the opening angle of the upper portion and to provide a resting orientation in the open configuration. At least a portion of the interior surfaces of the chamber defining the volume 408 are covered with the diffuse reflective material 210. In some embodiments, the material 210 is adhesive backed and applied to as many of the interior surfaces of the chamber as possible. The material may be implemented in one or more sheets or cutouts of material. Also illustrated is the aperture 216 to allow the light rays to enter the volume 408 and the sensor 220 (aperture 222 not visible).

In some embodiments, the upper portion 430 includes a lip 454 or edge that extends over an upper edge of the lower portion 432 to create an overlap to minimize light from escaping at the interface between the upper portion and the lower portion during treatment.

In several embodiments, a holding structure to position or locate the object to be treated within the volume is implemented at the interface of the upper portion and the lower portion. In this illustrated embodiment, the holding structure is implemented as two bushing assemblies 450 (which may be generically referred to as guide pieces) each having a channel 452 formed therein. Referring briefly to FIGS. 14A-15B, further details of the bushing assemblies 450 are discussed. The bushing assembly 450 includes a cover portion 1402 and a base portion 1404 that are hingably coupled with hinge 1406. Exterior end 1410 extends to an exterior of the lower portion 432 while interior portion 1412 extends to form a portion of the structure that defines the interior volume 408 of the chamber. In some embodiments, at least a portion of the interior portion 1412 is covered by a portion of the diffuse reflective material 210 (e.g., see the view of FIG. 6). In an open configuration (see FIGS. 14B and 15B) in which the bushing assembly 450 can receive a portion of the object to be treated, the cover portion 1402 is opened about the hinge 1406 to reveal the channel 452 extending from portion 1410 to portion 1412. A portion of the object to be treated in placed into the channel 452 of one or more of the bushing assemblies on either side of the volume. In some embodiments, catheter or other elongated object is inserted into the channels 452 of opposite bushing assemblies 450 to suspend the object within the volume 408 at or near the horizontal plan of the channels 452. In some embodiments, a light transmissive holding rod or wire is placed into the channel 452, the rod or wire extending across the volume 408 at the plane of the channel 452. The object may be rested on top of the rod or wire or rested on a light transmissive shelf affixed to the rod or wire. When at least a portion of the object and/or holding structure is within one or both channels 452, the cover portion 1402 is pivoted to a closed configuration (see FIGS. 14A and 15A) so that the portion of the object (e.g., catheter) and/or holding structure is retained within the channel/s 452 and protected from damage due to the closing of the upper portion 430 to the lower portion 432. The cover portion 1402 also protects the channel 452 and base portion 1404 from contacting the upper portion 430 of the chamber and getting damaged. Also, in the open position (FIGS. 14B and 15B), the cover portion 1402 interferes with the upper portion, preventing engagement of the door interlock and so preventing operation.

The dimensions of the components of the bushing assemblies 450 can be designed to loosely or snugly hold the portion of the object or holding structure. In some embodiments, the dimensions of the channel 452 are designed to be small enough to fit the object/holding structure while minimizing light treatment to escape the volume 408. Also, in the illustrated embodiment, a notch 1414 is formed in the base portion 1404 which allows a magnet 1408 affixed to an underside of the cover portion 1402 to extend at least partially therethrough to magnetically attract to a metallic portion of the lower portion 432. For example, in some embodiments, the upper and lower portions 430 and 432 are made from aluminum. In the closed orientation, the magnet 1408 retains the cover portion 1402 against the base portion 1404 regardless of the open or closed orientation of the upper portion 430 relative to the lower portion 432. Also, the cover portion 1402 includes a tab 1416 that allows the user to easily pull open the cover portion 1402, e.g., using a finger, to disengage the magnet 1408 from magnetic engagement with a portion of the lower portion 432. In the illustrated embodiment, the channels 452 are designed to hold the object to be treated at a central location within the volume 408. In some embodiments, each bushing could have multiple channels of the same or different widths and/or depths aligned in parallel or not. In some embodiments, more than two bushing assemblies 450 may be implemented at different portions of the lower portion 432 and/or may be implemented in the upper portion 430. In the illustrated embodiments, the bushing assemblies 450 remain with the stationary lower portion 432 of the chamber.

In the design of some embodiments, the bushing assemblies are replaceable. A variety of bushing assemblies are available with different channel sizes, to accommodate various catheter and other object sizes. A bushing with no channel is also available for applications where there is no catheter (e.g., hearing aids). The bushings are easily removed by the user. This allows a single system to be easily made compatible with a wide variety of objects for curing and/or sterilizing.

In some embodiments, an integrated controller is used to allow the user to specify the level of control during treatment and/or to allow for closed loop feedback as is more fully described through out this specification. In some embodiments, an integrated controller 470 allows several levels of user treatment control and selection. In some embodiments, the user can treat according to a time mode in which the user selects an amount of time to treat the object. In another embodiment, the user can treat according to a dose mode in which the user inputs the dose to be administered, e.g., in Joules per square centimeter, and the system treats until the dosage as measured using sensors has been completed. In another embodiment, the user can treat according to a manual mode in which the user starts the treatment and manually stops the treatment. In still another embodiment, the user can treat according to a time-varying irradiance profile, wherein the controller interfaces with the light source or a variable aperture to adjust the input optical power. The integrated controller may also control certain functions of the light source.

Figure 7:
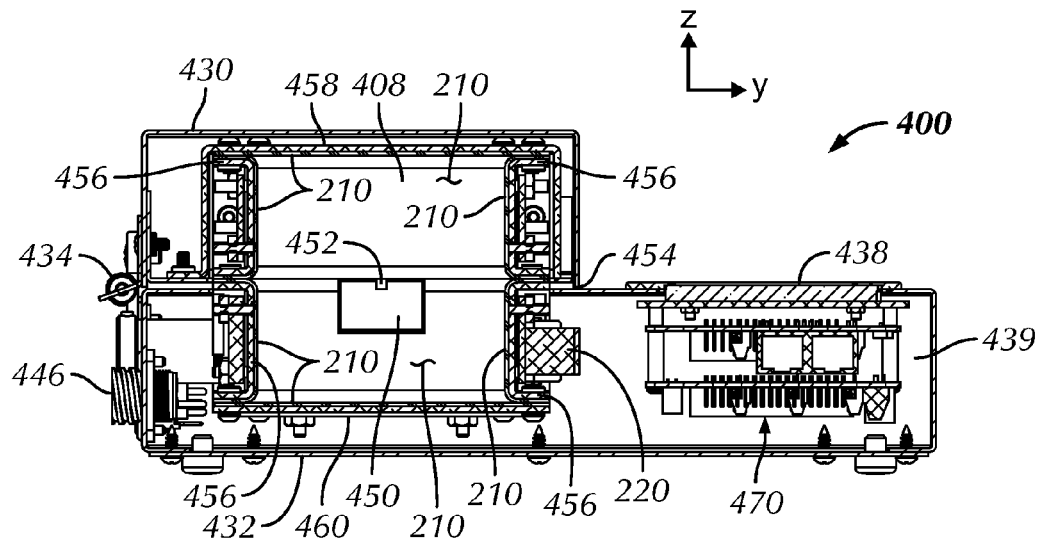
FIG. 7 is a side elevation cutaway view of the integrating optical system of FIG. 4 taken at plane B-B of FIG. 4 in accordance with several embodiments.
Figure 8:
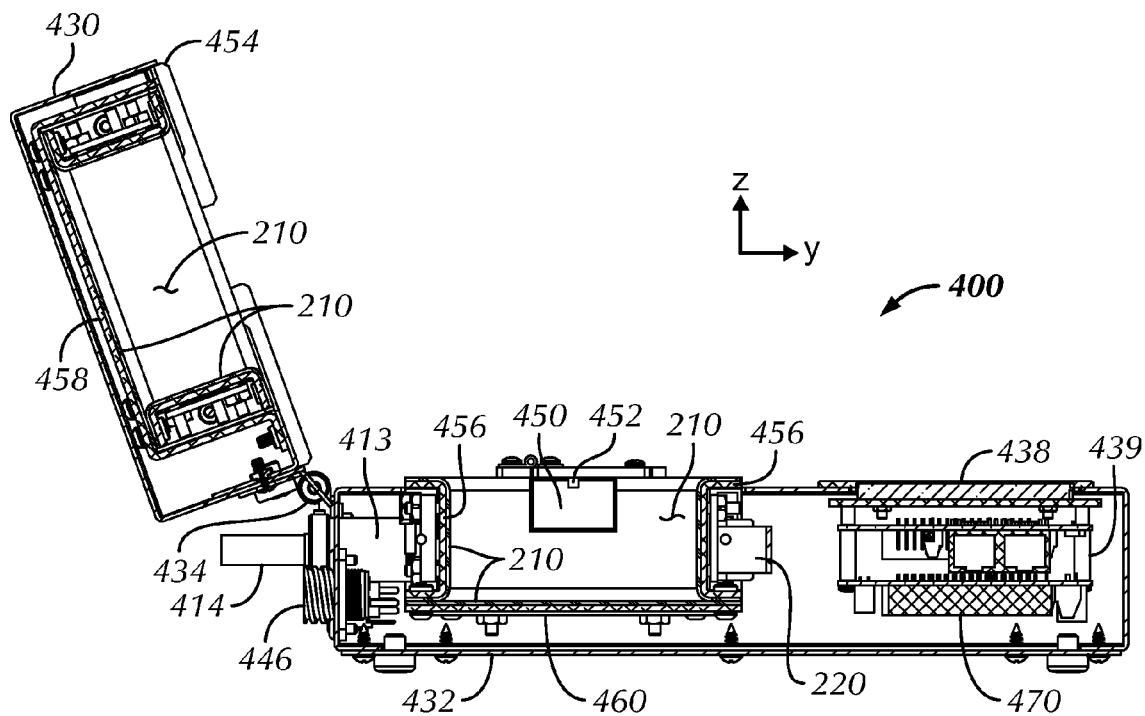
FIG. 8 is a side elevation cutaway view of the integrating optical system of FIG. 6 taken at plane D-D of FIG. 6 in accordance with several embodiments.
Figure 9:
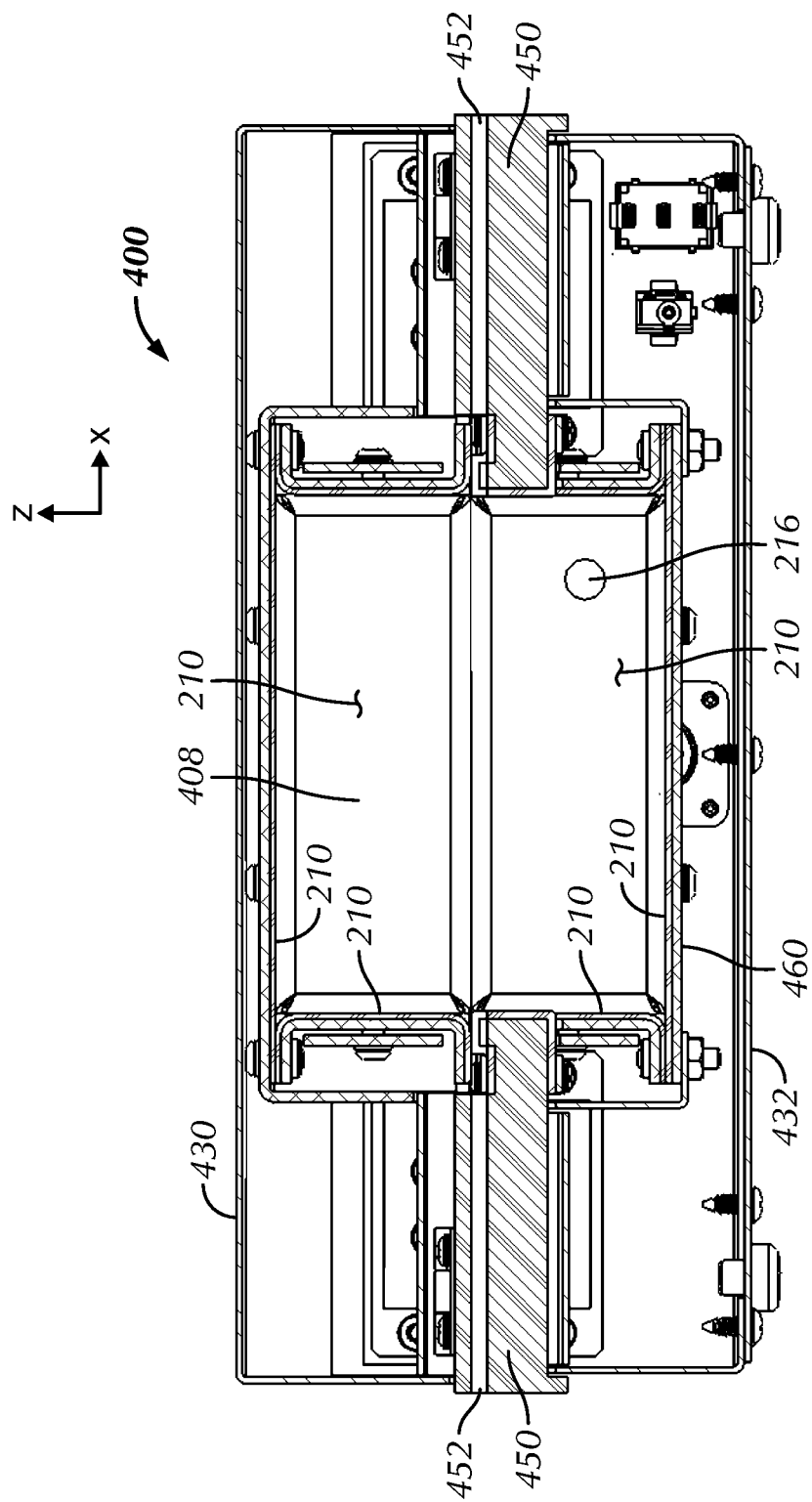
FIG. 9 is a front elevation cutaway view of the integrating optical system of FIG. 4 taken at plane A-A of FIG. 4 in accordance with several embodiments.
Figure 11:
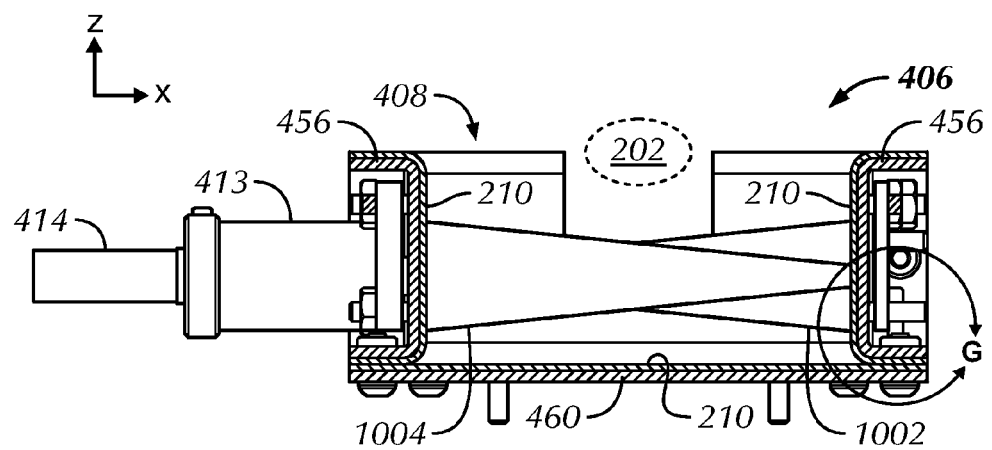
FIG. 11 is a side elevation cutaway view of one embodiment of the integrating optical chamber of FIG. 10 taken at plane E-E of FIG. 10 in accordance with several embodiments.
Figure 12:
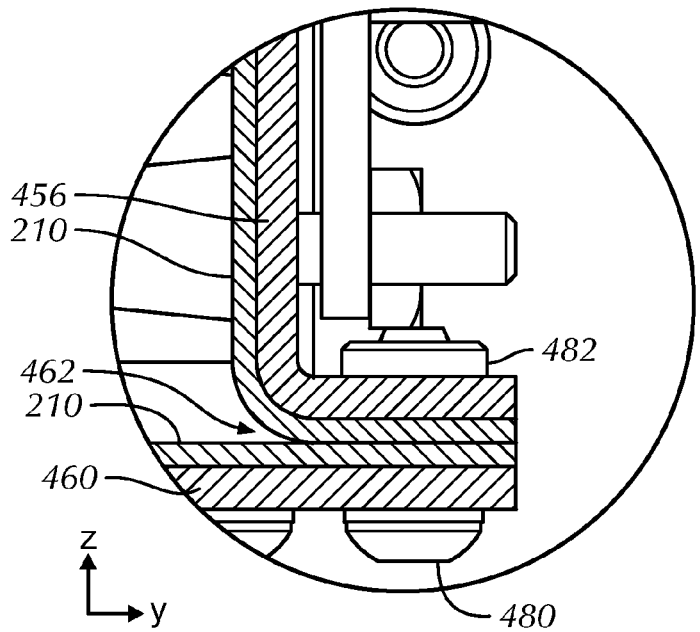
FIG. 12 is an enlarged side elevation cutaway view of a portion of the integrating optical chamber of FIG. 11 in accordance with several embodiments.

As illustrated in FIGS. 7 and 8 and also in the views of FIGS. 11 and 12, various panels or frames are used to form the structure of the integrating optical chamber having the volume. For example, each of the upper portion 430 and the lower portion 432 are formed with four side panels 456 and a top panel 458 (or a bottom panel 460). In one embodiment, the various panels are made of aluminum or other rigid material. At least a portion of the panels are covered with diffuse reflective material 210, e.g., the material 210 is adhered to the respective panels. The panels are fixed to each other using various fixing devices, e.g., screws, nuts, bolts, rivets, etc. In the illustrated embodiments, the side panels 456 curve into a horizontal top and bottom sections that fit against the top panel 458 and the bottom panel 460, respectively. A portion of the material 210 wraps around the curvature of the side panel 456. In the view of FIG. 12, the side panel 456 and the bottom panel 460 are fixed together in a manner to compress the diffuse reflective material in between. In some embodiments, the side panels and top/bottom panels are configured and held in position (e.g., using screws 480, nuts 482, bolts, etc.) to compress the diffuse reflective material 210 about 25 percent of its thickness (not illustrated) in order to minimize any corner or seam gap formed at location 462. As seen in FIGS. 6-9, the side panels 456 of the lower portion 432 have a cutout section to fit the interior portion 1412 of the bushing assembly 450. When the system 400 is in the closed configuration, the side panels 456 of the upper portion 430 and the lower portion 432 interface contact each other.

In some embodiments, the closing of the upper portion 430 causes the material 210 of the side panels 456 to compress against each other ensuring a tight fit (e.g., to prevent light from escaping at the interface of the upper and lower portions 430 and 432) between the upper portion and the lower portion. In some embodiments, one or more spring mechanisms may be implemented within one of both of the upper portion 430 and the lower portion 432 to apply a desired amount of pressure against the top panel 458 and/or bottom panel 460 to ensure that there is compression at the material 210 interface between the side panels 456 of the upper and lower portions 430 and 432. For example, in one embodiment, one or more spring mechanisms are located between an interior surface of the upper housing applying downward pressure against an upper surface of the top panel 458, which in turn applies a downward pressure on the side panels 456 of the upper portion 430, which in turn ensures downward pressure of the side panels 456 to the side panels of the lower portion 432 when the system is closed.

Figure 10:
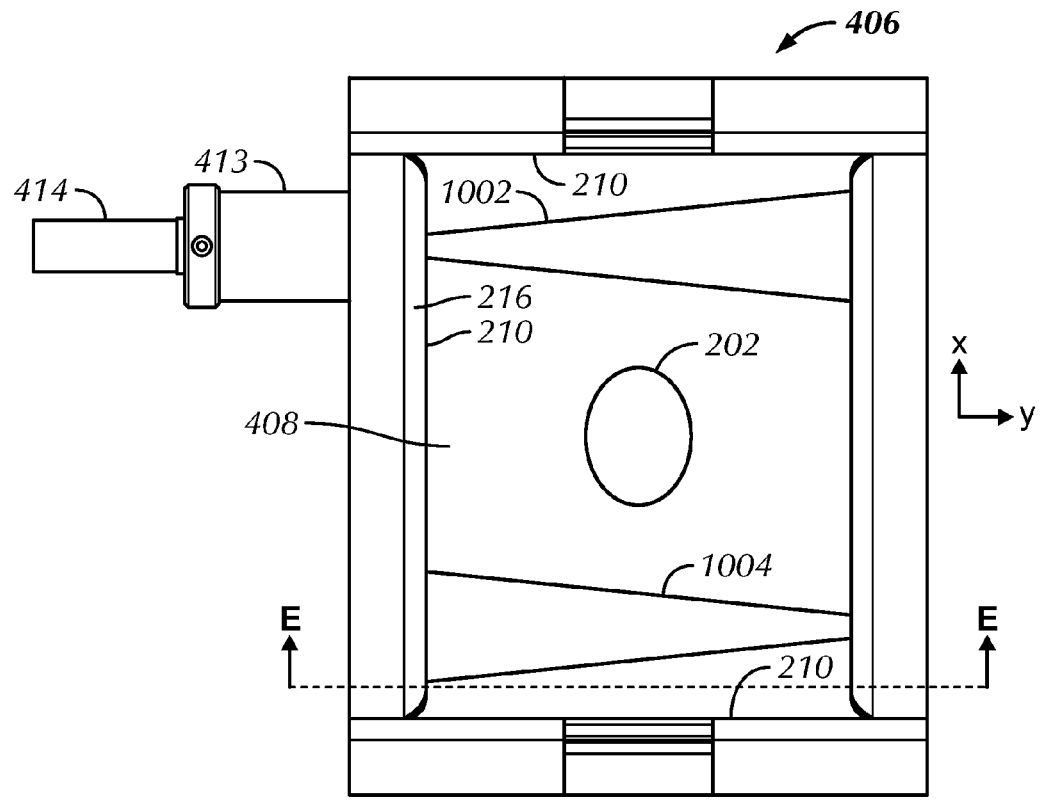
FIG. 10 is plan view of a bottom portion of the integrating optical chamber of the integrating optical system of FIG. 6 illustrating incident light entering the chamber and a field of view of an optical sensor in accordance with several embodiments.

Referring next to FIG. 10, an entry path 1002 of direct light rays from the aperture (e.g., shown as diverging) is directed to strike an interior surface of the chamber 406 and be diffusely reflected. In this way, no rays of light are incident on the target 202 without being diffusely reflected at least once. Furthermore, a sensor field of view 1004 is shown such that the sensor can only sense light rays that have been diffusely reflected at least two or more times. As illustrated in FIG. 10, the sensor field of view is horizontally offset from the entry light path 1002, and as seen in the embodiment of FIG. 11, is generally in vertical alignment with the entry light path 1002 and below the object 202. It is understood that there are other configurations possible that will provide that the direct light rays in the entry light path are not incident on the object 202, and that the sensor field of view does not include any direct light rays from the entry light path. As will be described in more detail below, the sensor field of view 1004 is located and configured such that the light sensed corresponds to the light that is incident on the object itself. In some embodiments, the sensor 220 is a photodiode sensor that produces an output proportional to the power incident on the diode. Since the sensor field of view 1004 is fixed, the output is proportional to the exitance from the chamber wall. The object 202 being cured is not in the field of view of the sensor. However, due to the integrating nature of the chamber (by design), the incidence on the object is proportional to the wall exitance. Therefore, the sensor output is proportional to the radiation incident on the object. It is also noted in some embodiments, the sensor may detect light transmitted through the diffuse reflective material (e.g., the sensor is positioned behind the diffuse reflective material at an aperture in the chamber wall that is covered by the diffuse reflective material) rather than be coupled to an opening in diffuse reflective material, and in such embodiments a second aperture in the diffuse reflective material is not needed and losses due to such second aperture are avoided. Also, when the sensor is behind the diffuse reflective material, the sensor may be placed in multiple locations since the field of view of the sensor is the back side of the material 210, not into the volume 208.

Figure 13:
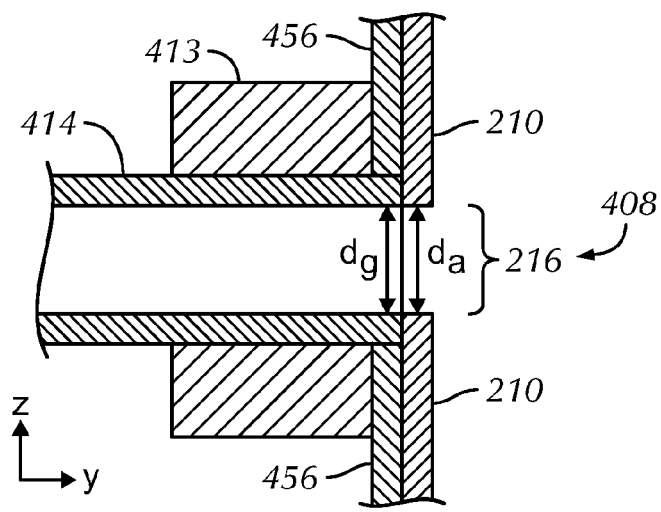
FIG. 13 is a side elevation cutaway view of a light coupler coupling a light guide to an aperture of an integrating optical chamber in accordance with several embodiments.
Figure 14B:
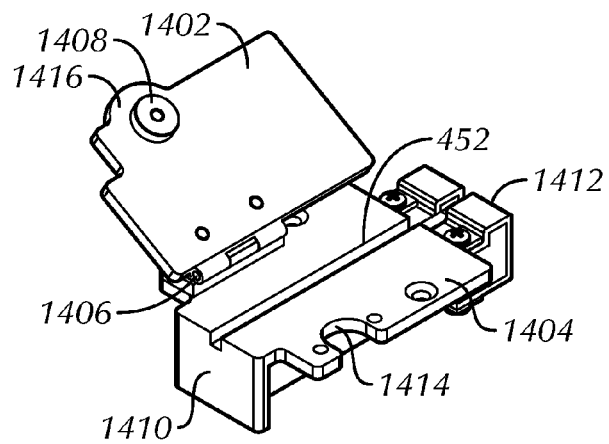
FIGS. 14A and 14B are above perspective views of a bushing assembly of the integrating optical system of FIG. 4 in open and closed configurations, respectively, in accordance with various embodiments.
Figure 14A:
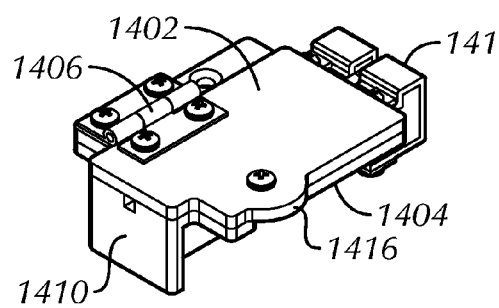
Figure 15B:
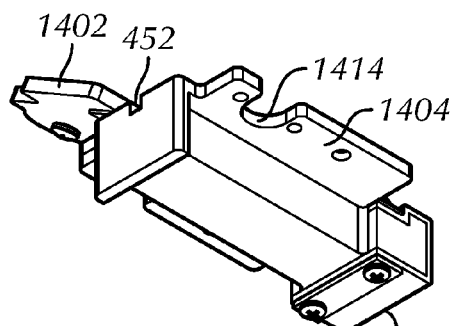
FIGS. 15A and 15B are below perspective views of the bushing assembly of FIGS. 14A and 14B in open and closed configurations, respectively, in accordance with various embodiments.
Figure 15A:
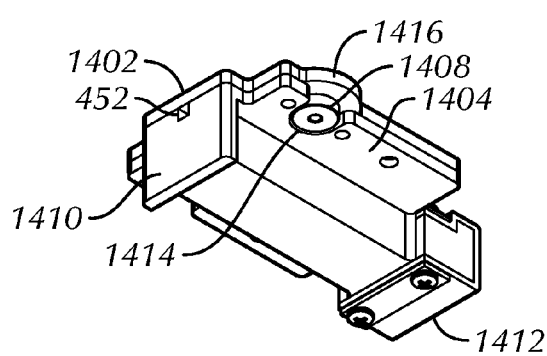

As illustrated in FIG. 13, in some embodiments, the light guide 414 is mated to the aperture 216 such that the end of the light guide 414 is nearly flush with or slightly recessed (as illustrated) from the plane of the material 210. In some embodiments, this is done in order to minimize non-diffusely reflected surfaces within the volume 408. In some embodiments, the diameter of the aperture 216, $D_a$, is designed relative to the diameter of the light entry port of the light guide, $D_g$. For example, in some embodiments, the aperture diameter is a factor K of the light guide diameter. That is, in some embodiments, $D_a = K \times D_g$, where $0.5 \leq K \leq 5$. In some embodiments, it is preferred to have the aperture diameter slightly larger than but closely match that of the light guide to maximize light transfer and avoid locations for light to escape the volume or reflect off of the aperture before entering the volume 408. It is noted that in some embodiments, although not shown, a window, filter, shaping optics and/or shutter may be implemented at the aperture and/or within the light guide. It is also noted that the entry path of light may be diverging, converging or collimated. In the design of some embodiments, the light guide connector is designed to be easily removed by the user. Connectors of various sizes may be used, depending on the light guide diameter being used. This allows a single system to be easily made compatible with the wide variety of light guides in use.

Figure 16:
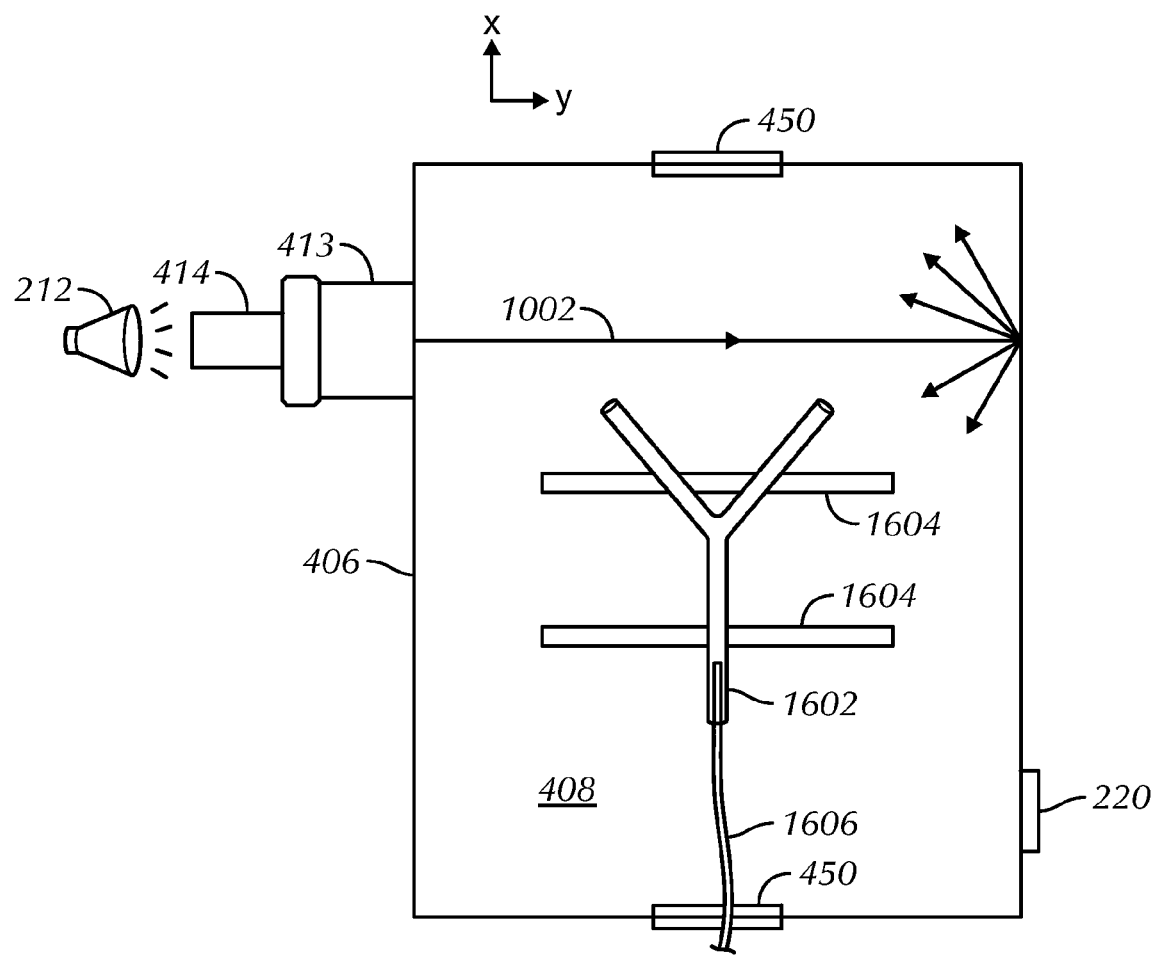
FIG. 16 is a schematic diagram illustrating an integrating optical chamber illustrating an input light guide, a sensor device, a light treatable object and a holding structure in accordance with several embodiments.

Referring next to FIG. 16, a similar view to that shown in FIG. 10 is illustrated but provides an alternative holding structure in accordance with several embodiments. In this case, the object to be treated, e.g., cured, is a Y connector 1602 in which a catheter 1606 or IV tube will be cured to different portions of the connector 1602. UV curable adhesive is applied to the catheter 1606 which is inserted into the connector 1602. The connector is then placed on supports 1604 and the catheter extends out of the volume 408 via the channel 452 of a bushing assembly 450. The supports 1604 in this case are light transmissive walls or pillars upstanding from a floor of the chamber. Other catheters may be cured into other portions of the connector and routed out of the volume using bushing assemblies. Alternative holding structures include shelves, tables, wires, rods, mats, etc.

Figure 17:
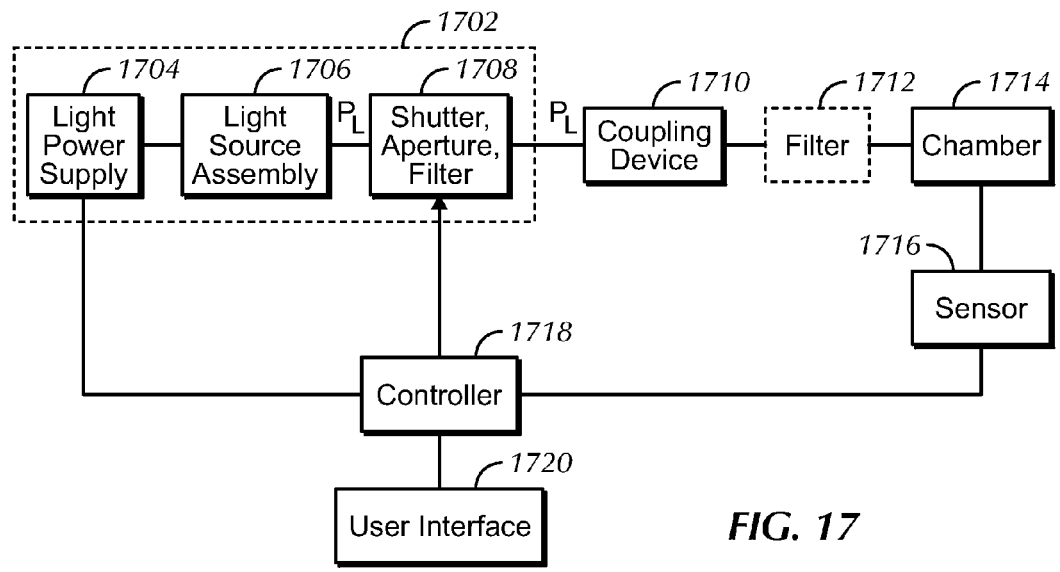
FIG. 17 is a functional block diagram of the components of an integrating optical system in accordance with several embodiments.

Referring to FIG. 17, shown is a functional block diagram of the components of an integrating optical system in accordance with several embodiments. The system comprises a light source unit 1702 including a light source (e.g., lamp/s, LED/s, laser/s, etc.) power supply 1704, a light source assembly 1706 and optional shutter, aperture, and/or filter 1708. A light coupler 1710 such as a light guide, couples light from the light source assembly 1706 to an integrating optical chamber 1714 either directly or via a filter 1712. The path of light is indicated as $P_L$. Uniform diffusely reflected light is sensed by sensor 1716 which communicates information to and is controlled by a controller 1718. A user interface 1720 is coupled to the controller to allow a user to program and operate the system. The user interface may include one or more of a display screen and a user input feature (such as one or more buttons, dials, knobs, and/or touch sensitive display screens). The controller 1718 also controls the light power supply 1704 and the shutter, aperture and/or filter 1708. In some embodiments, an amount of light incident on the object is controlled using feedback from the sensor 1716 and adjustments made to the light power supply 1704 and/or the shutter, aperture and/or filter 1708 to deliver a certain dosage or treatment time. The controller may be implemented within the system, e.g., within the lower portion 432 of FIGS. 4-9 or be external to the housing and couple thereto.

Figure 18:
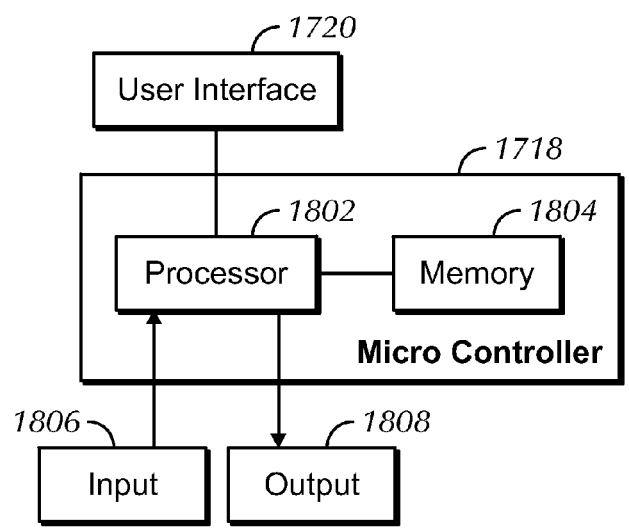
FIG. 18 is a functional block diagram of an exemplary controller for use with an integrating optical system in accordance several embodiments.

FIG. 18 is a functional block diagram of an exemplary controller for use with an integrating optical system in accordance several embodiments. The controller 1718 may be implemented as a processor based system including a processor 1802 and a memory 1804 (also referred to as a computer readable medium), a user input 1806, an output 1808 and a user interface 1720. The input 1806 allows data, signals and/or instructions to be coupled to the processor 1802, e.g., sensor 1716 data may be coupled to the processor and memory via the input. Additionally, the input may be used for external commands or signaling from an external computer device or network to be received at the processor. The output may be used to output control signals to one or more components of the system, such as to the light source power supply or shutter, or to an external computer device, printer, display or external network. The user interface allows the display of information and menus and well as the receipt of user entered programming information or parameters. In some embodiments, executable program code is stored in the memory 1804 that when executed by the processor performs one or more functions in operating and controlling light treatment using the system. The memory 1804 may be one or more random access memories or read only memories, hard disk drive, flash memory device, etc. The functionality of the controller may be implemented using one or more of hardware, software and firmware.

A general operation of an integrating optical system, such as that of FIGS. 4-18, with respect to the assembly and treatment of catheters according to some embodiments is as follows. It is generally assumed that the integrating optical system 400 or other system is in a ready state. First the upper portion 430 is opened from the lower portion 432 to reveal the chamber having the volume 408. Then, the cover portion 1402 of the bushing assemblies 450 is opened and a catheter is placed in the channels 452 of adjacent bushing assemblies 450 such that the portion to be cured is centrally located within the volume 408. The cover portion 1402 is closed over the catheter to secure the object. Next, the assembly is assembled, e.g., by sliding a balloon over the catheter end. UV curable material is dispensed as needed and then the upper portion 430 is closed over the lower portion 432. It is noted that in some embodiments, in order to reduce damage due to excessive curable material that spills onto the floor of the chamber, an additional sheet of material 210 may be positioned on the floor of the chamber to diffusely reflect light and to also be removed if there are significant spills. The integrating optical system is then operated to begin the curing process. This may be done several ways according to different embodiments. For example, by (1) manually turning the lamp on (or opening the lamp shutter), (2) pressing a RUN button on the control system or (3) the controller is configured to start a cure cycle once it senses the door is closed.

In different embodiments, completing the cure may be done in one of several ways, for example, by manually de-energizing the light source and/or shutter or opening the upper portion 430 when desired. The door interlock will cause the light source (shutter) to de-energize. In another example using time exposure control, the controller may be used to expose the object for a user-input duration. Once the exposure time is reached, the controller will de-energize the light source (shutter). In another example using dose exposure control, the controller may be used to expose the object until a user-input dose (energy per unit area) is reached. The chamber sensor 220 output, having previously been calibrated, is integrated over time producing a signal indicating the dose exposure of the object. When the dose indicated by the integrated sensor signal matches the user-input dose target, the controller de-energizes the light source (shutter). Once complete, the upper portion 430 and cover portion 1402 are opened and the cured object is removed.

In accordance with one or more embodiments, one or more of the following features and benefits apply. In some embodiments, substantially uniform irradiation of small devices may be accomplished by use of diffusely reflecting material in an integrating optical chamber. The diffusely reflecting material is configured to surround the object and thru multiple diffuse reflecting interactions generate a highly uniform light field at the object that is excited by one or more lamps remotely located from the object such that most of the light incident on the object is reflected from the diffuse reflecting material at least once prior to striking the object. In one or more embodiments, this substantially uniform irradiance of an object may be independent of the light source type (light guide, arc lamp, LED, laser) and location relative to object. In some embodiments, a substantially uniform illumination system is combined with part fixturing, which allows part assembly, adhesive dispensing and curing to be done without moving the object or part.

Some embodiments allow in situ measurement of irradiance at object with object in place, regardless of whether or not the measurements are used to make adjustments. This is in contrast to known systems that can only measure the light input to or out of a light guide. In an integrating optical system, any components within the volume potentially alter the amount of light diffusely reflecting and integrating. That is, the object size and other characteristics influence the object incidence. This influence is related to the wall exitance, which is measured. Therefore, in some embodiments, the measurement provides true reading of object incidence regardless of object features or impact on chamber irradiance.

In some embodiments, described more thoroughly below, a closed loop feedback control system at least measures exitance from one or more walls of the chamber; relates that exitance to incidence on the object; calculates the dose received by the object (time integral of object incidence); and terminates the exposure once the desired dose is achieved.

In some embodiments, control of irradiance and dose is accomplished using feedback of actual measured irradiance at the object with the object in place measured in real time. Again, this is allowed by the use of integrating chamber, not just a feature of the control system.

Figure 28:
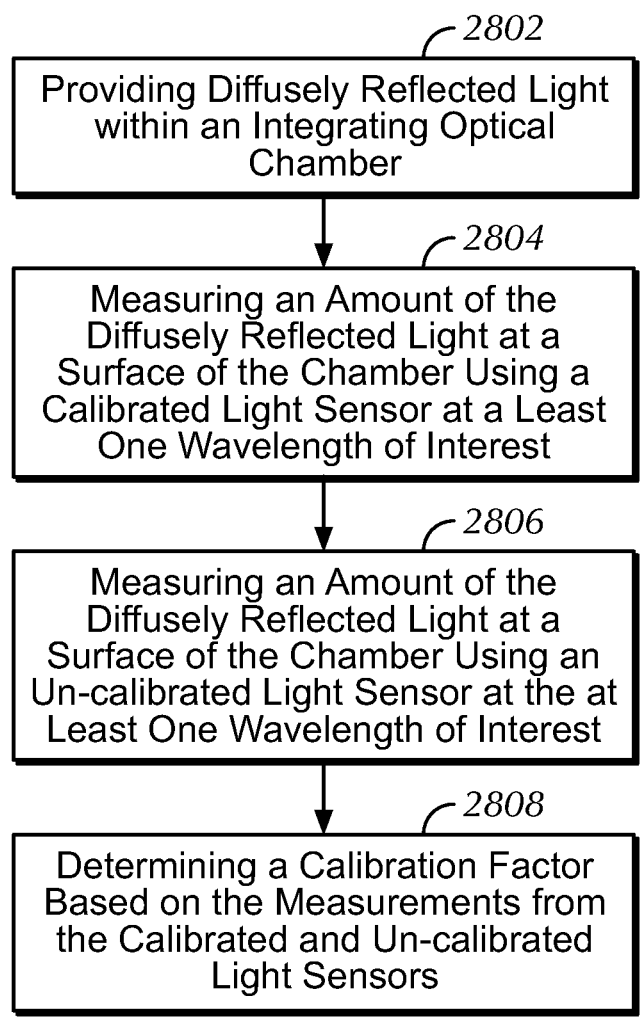
FIG. 28 is a flowchart illustrating a method for use in calibrating an uncalibrated light sensor for use in an integrating optical system in accordance with several embodiments.

In some embodiments, methods are provided to calibrate the feedback signal (see FIG. 28 for example). The feedback is usually a voltage derived from a photodiode whose output is proportional to the incident optical power. In some embodiments, the sensed voltage is to be related to the exitance of the chamber walls in watts per unit area. In one embodiment, a calibrated sensor (such as a radiometer or spectrometer) is used to measure the wall exitance ("$E_{CAL}$") within the volume. At the same time (or at least under the identical conditions if not at the same time), record the output of an uncalibrated photodiode sensor being used ("$V_{PD}$"). A calibration factor is determined as the ratio of the two ($E_{CAL}/V_{PD}$). This calibration value is recorded in controller memory. During treatment or cure, the object incidence is the product of sensor output and calibration factor. In one case, the dose is the time integral of the sensor output and calibration factor product.

In some embodiments, the control system may also measure the exitance from one or more walls of the chamber and adjust the light power input to the chamber (or other parameters such as described herein) in order to keep the object incidence constant as the input source power change due to aging or other factors. The power may be adjusted (i.e., to adjust an amount of light incident on the object over time (as a dose) a variety of ways, for example and not limited to these examples, by doing one or more of the following (a) adjusting the bulb input power, (b) adjusting the power coupled to the chamber, for example (i) with a variable aperture between the source and chamber, (ii) with a variable transmission element between the source and chamber, (iii) by changing the optical power coupled to the chamber, for example, by focusing less light thru the input port.

Figure 19:
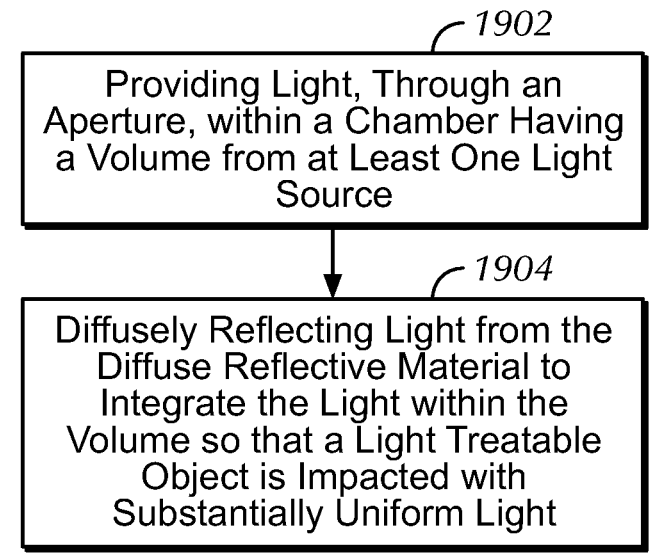
FIG. 19 is a flowchart illustrating a method of impacting a light treatable object with substantially uniform light originating from a light source in accordance with several embodiments.

Referring next to FIG. 19, shown is a flowchart illustrating a method of impacting a light treatable object with substantially uniform light originating from a light source in accordance with several embodiments. In some embodiments, this method may be performed by one or more integrating optical systems described herein or other systems. Initially, light is provided through an aperture within a chamber having a volume from at least one light source (Step 1902). Then, the light is diffusely reflected using diffuse reflective material to integrate the light within the volume so that a light treatable object is impacted with substantially uniform light (Step 1904). In some embodiments, the light is used to cure and/or sterilize a portion of the light treatable object. In different embodiments, substantially uniform light is light having less than 2% non-uniformity, less than 5% non-uniformity and less than 20% non-uniformity, respectively. In another embodiment, substantially uniform light is light having an incidence of an object that does not differ by more than plus or minus 5%. In some embodiments, the light incident on the light treatable object has an incidence (e.g., as measured within the chamber) between about 10 and 10,000 mW/cm². In other embodiments, the light incident on the light treatable object has an incidence between about 100 and 3,000 mW/cm². In further embodiments, the light incident on the light treatable object has an incidence between about 10 and 1,500 mW/cm². In one specific embodiment, the light has an incidence of approximately 240 mW/cm².

Figure 20:
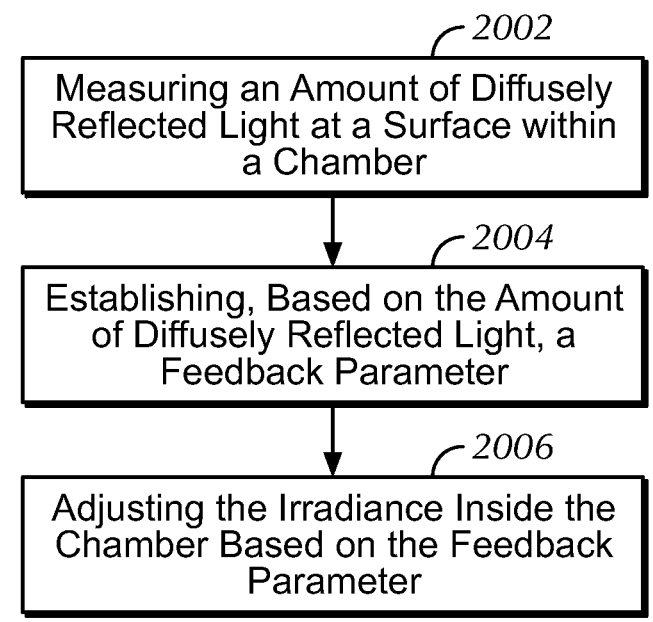
FIG. 20 is a flowchart illustrating a method of adjusting the irradiance in an integrating optical chamber based on a feedback parameter established based on an amount of diffusely reflected light in accordance with several embodiments.

Referring next to FIG. 20, shown is a flowchart illustrating a method of adjusting the irradiance in an integrating optical chamber based on a feedback parameter established based on an amount of diffusely reflected light, the light being used to treat a light treatable object at least partially contained within the chamber, in accordance with several embodiments. In some embodiments, this method may be performed by one or more integrating optical systems described herein or other systems.

First, an amount of diffusely reflected light is measured at a surface within a chamber (Step 2002). The light measured at the surface within the chamber may be referred to as the exitance of the light from the surface within the chamber, where exitance is generally the light irradiance exiting a surface. In several embodiments, exitance refers to the irradiance of diffusely reflected light at an inner surface of the chamber at a sensor field of view. For example, this measurement is taken with a calibrated sensor (e.g., sensor 1716 of FIG. 17) and may typically be provided as an irradiance in units of W/cm² (or mW/cm²). Next, a feedback parameter is established based on the measured amount of diffusely reflected light within the chamber, the feedback parameter being proportional to an incidence on at least one light treatable object within the chamber, the diffusely reflected light being integrated within the chamber to provide the irradiance comprising substantially uniform light (Step 2004). Generally, incidence as used herein refers to the irradiance of light incident on or impacting the light treatable object. In some embodiments, the feedback parameter is a function of the output of the sensor/s (e.g., photodiodes that output a voltage that is proportional to the incident optical power) measuring the light (e.g., the feedback is the output of the sensor/s). In some embodiments, the feedback parameter is the output of the sensor/s multiplied by a multiplier, such as a constant or a function. In some embodiments, this multiplier corresponds to a property of the sensor/s measuring the light. For example, if the sensor has a linear response, the multiplier may be a constant multiplier. If the sensor has a non-linear response, the multiplier may be a non-linear multiplier. In some embodiments, the feedback parameter is integrated over time, whereas in other embodiments, it is not integrated over time. In some embodiments, for example, the feedback parameter is established at one or both of the sensor 1716 and the controller 1718 of FIG. 17. For example, in some embodiments, the sensor output is used directly as the feedback parameter; thus, the feedback parameter is established at the sensor. It is understood in the art that a typical sensor may include photodiode/s and any supporting electronics or circuitry such as an amplifier to provide the photodiode output as a signal suitable for use by other devices. In another example, the sensor output is provided to a controller (e.g., controller 1718) which adjusts (e.g., modifies, multiplies, scales, and so on) the sensor output to result in the feedback parameter; thus, the feedback parameter is established at the controller.

According to several embodiments, there is a relationship between the measured light exitance at a surface of the chamber and the light incidence on the object. In some embodiments, the measured exitance is assumed to equal the incidence on the object. In some embodiments, the incidence on the object is the measured exitance multiplied by a factor, e.g., where the factor is a value between 0.5 and 6. The more transparent the object is, the higher the factor (e.g., an object with high transparency may have a factor of 6). If the object is light absorbing, the object will likely have a factor of 3 or less. If it is assumed that the incidence is the same as the exitance, the factor would be 1. Additionally, in some embodiments, the geometry and orientation of the object within the chamber can alter the factor used. That is, an object having a surface that is oriented to only see or view one interior wall of the chamber will have a factor at or near 1, whereas a surface of the object visible to more than one interior wall of the chamber will have a higher factor. Likewise, a recess or other portion of the object that is not directly visible to any interior surface of the chamber may have a factor less than 1. In some embodiments, the factor is used in calculating or estimating the incidence (integrated over time or not) on the object based on the exitance as measured in the chamber. In other embodiments, the specific factor is not considered; however, it is understood that the measured exitance relates to the incidence on the part. In some embodiments, the factor is generally the same for each point on the surface of the object, e.g., the incidence on the object is generally uniform.

Next, the light irradiance inside the chamber is adjusted based on the feedback parameter (Step 2006). In some embodiments, the amount of light or light dose received at the object is adjusted in the chamber and/or a parameter of the light treatment (e.g., affecting the amount and/or wavelengths of light received per unit time) is adjusted. In different embodiments, this irradiance adjustment may be effected in one or more ways, including, but not limited to: (a) adjusting the time exposure of the object e.g., by terminating the light treatment once a target dose (e.g., in terms of Joules/cm$^2$) has been reached or at a time other than when treatment would be normally terminated, i.e., this effectively alters the overall light dose received at the object; (b) adjusting the power of the light source power supply; (c) adjusting the light power coupled to the volume of the chamber after the light has been generated by the light source, for example, (i) with a variable aperture between the source and chamber (e.g., at the source, between the source and a light guide to the chamber, at an aperture of the chamber, and so on), (ii) with a variable transmission element between the source and chamber (e.g., at the source, between the source and a light guide to the chamber, at an aperture of the chamber, and so on), (iii) by changing the optical power coupled to the chamber, for example, by focusing less light thru the input port (i.e., making adjustments to the reflector or other focusing optics); and (d) adjusting the wavelengths of light passing into the chamber (e.g., using one or more positionable spectral filters). In some embodiments, the amount of light or light dose received at the object is adjusted by introducing or removing optical absorbing elements into/out of the chamber and/or creating one or more selectably sized openings in the chamber to reveal optical absorbing element/s or to reveal an open area via a selectable exit port so that the chamber irradiance is reduced/increased by the added/adjusted loss area and/or added/adjusted open area. Added or adjusted loss areas and/or open areas will reduce or adjust chamber irradiance in accordance with integrating sphere theory (see further description below). In some embodiments, the light is used to cure and/or sterilize a portion of the light treatable object. In some embodiments, the adjustment is controlled by the controller 1718 of FIG. 17.

Briefly referring to the system 3000 of FIG. 30, in some embodiments, one or more elements 3002 are selectively introduced and removed into and from the chamber volume 208 to adjust irradiance in the chamber (e.g., based on the feedback parameter). Although one element 3002 is shown, more than one element may be used. In one embodiment, the element 3002 is normally contained with a recess 3004 or opening, then actuated (e.g., using a controller or other actuator, not shown) to physically extend or move a selectable amount into the chamber volume (e.g., moved in the direction of arrow 3006). The introduction of the element provides a loss area within the volume that will result in a change of irradiance in the chamber. Generally, the element 3002 may be any material or structure that is at least partially absorbing in the wavelengths of interest. In some embodiments, the element 3002 may be an absorbing (e.g., black) surface, or may be partially transmissive or partially reflective or partially absorptive. For example, the element 3002 may be a plastic, glass, or metal object. In some cases, the element 3002 is selectively transmissive or selectively reflective or selectively absorptive, e.g., the element may be PYREX glass, which transmits light having wavelengths greater than about 300 nm, but blocks light having wavelengths less than about 300 nm. In one form, the element is a thin plate or sheet that is selectively extended into the volume 208 through an opening or slot. In some embodiments, the element may include a diffuse reflective material on the surface exposed to the volume so that when in the retracted position, the element 3002 does not introduce a loss. In some embodiments, the element 3002 is contained behind a door that is opened so that the element may be introduced into the volume. In some embodiments, diffuse reflective material is positioned tightly along one or more of the edges about the element, the recess, a door, and so on to minimize losses when losses are not intended. In some embodiments, the element 3002 is located within the volume so that it is not receiving light directly from the light input and is not blocking the field of view of a sensor 220. The other components of the system 3000 of FIG. 30 in common with the system 200 of FIG. 2 have the same functionality and discussion is thus not repeated for FIG. 30.

In some embodiments, still referring to FIG. 30, instead or in addition to use of the element 3002, element 3010 is positioned external to the chamber so that chamber radiation exiting an opening 3016 in the chamber wall created by a door 3012 or similar (e.g., a cover, variable aperture window, etc.) is incident on the element 3010, resulting in a reduction of chamber reflecting surface area ($A_p$ in Eq. (2) below) and absorbing the exiting optical energy on the element 3010. For example, door 3012 is normally in a position to cover the element 3010, but can be selectively actuated or moved (e.g., in the direction of arrow 3014 using a motor, actuator or controller (not shown)) to create a variable sized opening 3016 revealing at least a portion of the element 3010. The position of the door 3012 causes the opening 3016 to be of a selective size, creating a selectably sized loss area at a selectable port of the chamber. The element 3010 may be variably implemented in form, material, transmissivity, etc., as described in connection with the element 3002. In some embodiments, the interior surface of the door 3012 facing the volume 208 is coated or covered with diffuse reflecting material. In some embodiments, no element 3010 is needed, but the opening 3016 is created to allow radiation to exit the chamber such that the exiting radiation is dispersed into the surrounding environment outside the chamber. That is, in these embodiments, there is no element 3010 behind the door 3012. This creates a variably sized open area via a variably sized exit port.

Generally, according to known integrating sphere theory, the irradiance of the diffusely reflected light inside the chamber is the power of the light per unit area. The power or flux of the light in an integrating sphere can generally be expressed in units of power (e.g., watts) as:

$$= \Phi_i \rho \left( \frac{A_s - A_i - A_e}{A_s} \right) \qquad \text{Eq. (1)}$$

where $\Phi_i$ is the input flux, $\rho$ is reflectance, $A_s$ is the total surface area in the chamber, $A_i$ is the input port area and $A_e$ is the exit port area of the chamber [See page 4 of LABSPHERE, "A Guide to Integrating Sphere Theory and Applications, Tech Guide," published at least on or before Nov. 12, 2009, pp. 1-19, Labsphere Inc., North Sutton, N.H., which is incorporated herein by reference]. In some embodiments, this equation for the flux or power (e.g., in units of watts) is alternatively expressed as:

$$= \Phi_i \rho \left( \frac{A_s - A_p - A_L}{A_s} \right) \qquad \text{Eq. (2)}$$

where $\Phi_i$ is the input flux, $\rho$ is reflectance, $A_s$ is the total surface area in the chamber, $A_p$ is the area of all ports (e.g., input and exit ports) and $A_L$ is the area of all loss portions in the chamber (e.g., absorbing material, non-reflecting surfaces, etc.). In the embodiment of FIG. 30, the element/s 3002 are incorporated in Eq. (2) in $A_L$ such that $A_L$ can be selectively changed to alter the flux in the chamber, which results in a change of irradiance in the chamber. In further embodiments of FIG. 30, opening/s 3016 in the chamber (to reveal element 3010 or to reveal an exit port) are incorporated in Eq. (2) in $A_p$ such that $A_p$ can be selectively changed to alter the flux in the chamber which results in a change of irradiance in the chamber.

Referring back to FIG. 20, as used throughout this specification, in some embodiments, irradiance or incidence of the light treatment can be measured or expressed in terms of $W/cm^2$ (or $mW/cm^2$), whereas the dose or time integral of the irradiance is expressed or measured in terms of $J/cm^2$ (i.e., Joules/$cm^2$). The feedback control techniques to adjust irradiance in the chamber of one or more embodiments can be used to adjust one or both of the incidence and dose.

In some embodiments, this method implements a closed loop feedback control system that measures exitance (e.g., $mW/cm^2$) from one or more walls of the chamber; relates that exitance to incidence on the object; calculates the dose received by the object (time integral of object incidence, e.g., $J/cm^2$); and terminates the exposure once the desired dose is achieved.

Figure 21:
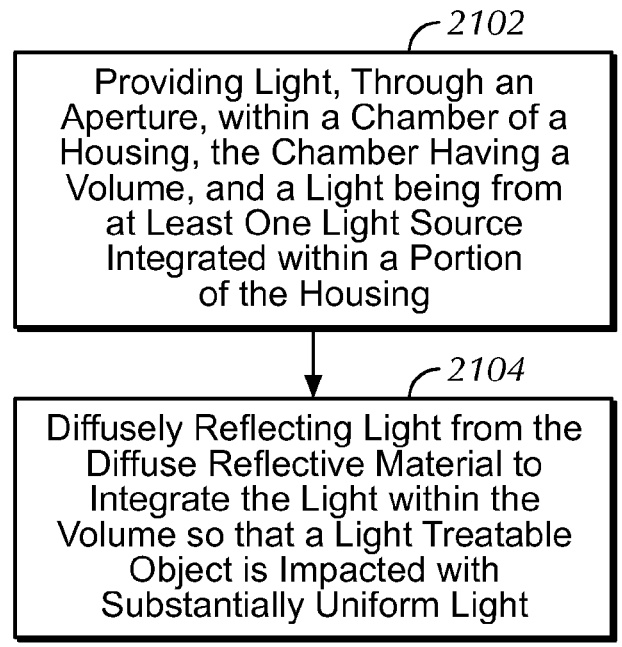
FIG. 21 is a flowchart illustrating a method of impacting a light treatable object with substantially uniform light originating from an integrating optical system having an integrated light source in accordance with several embodiments.

Referring next to FIG. 21, shown is a flowchart illustrating a method of impacting a light treatable object with substantially uniform light originating from an integrating optical system having an integrated light source in accordance with several embodiments. In some embodiments, this method may be performed by one or more integrating optical systems described herein or other systems. First, light is provided through an aperture within a chamber of a housing, the chamber having a volume, and the light being from at least one light source integrated within a portion of the housing (Step 2102). Next, light is diffusely reflected from diffuse reflective material to integrate the light within the volume so that a light treatable object is impacted with substantially uniform light (Step 2104). In some embodiments, the light is used to cure and/or sterilize a portion of the light treatable object.

Figure 22:
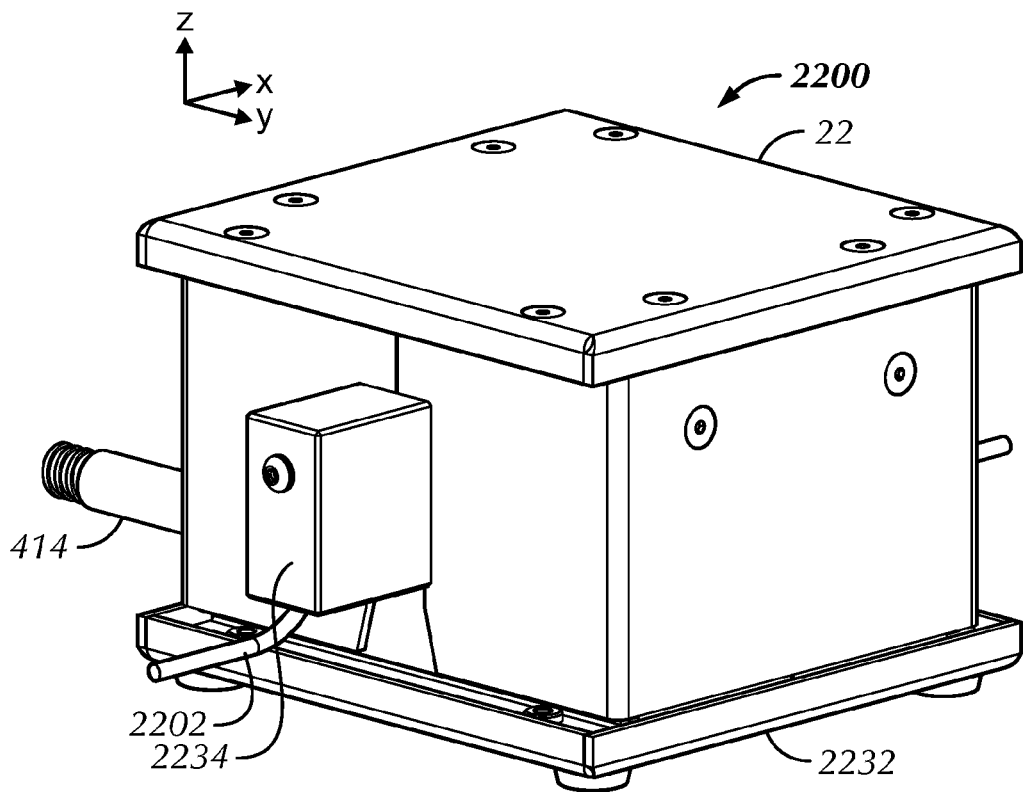
FIG. 22 is a front perspective view of an integrating optical system comprising a housing including separable portions in a closed configuration in accordance with several embodiments.
Figure 23:
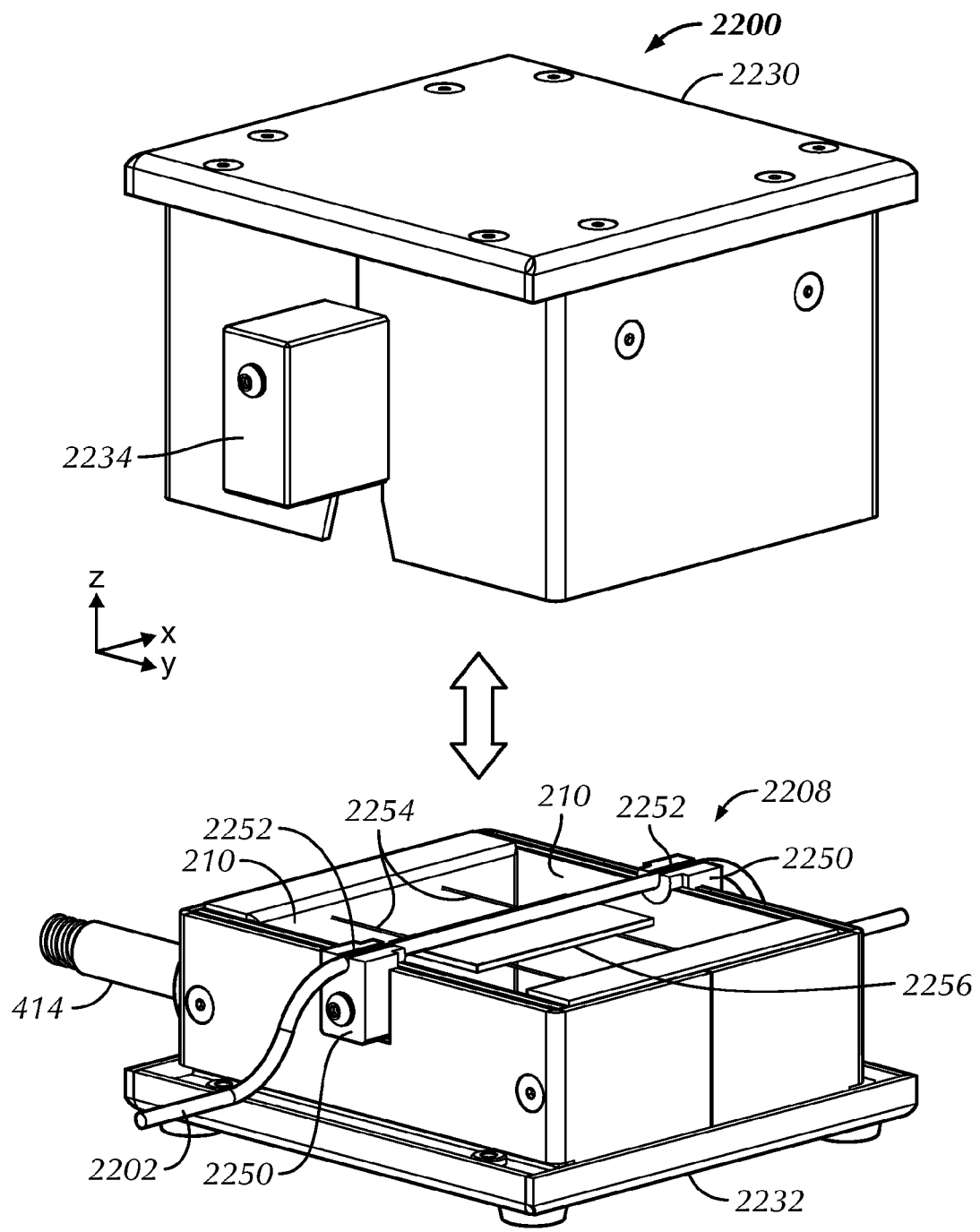
FIG. 23 is a front perspective view of the integrating optical system of FIG. 22 in which the separable portions are in an open configuration exposing portions of a volume of the integrating optical chamber in accordance with several embodiments

Referring next to FIGS. 22 and 23, are two views of an integrating optical system 2200 comprising a housing including separable portions in both open and closed configurations in accordance with several embodiments. The housing includes an upper portion 2230 and a lower portion 2232. The upper portion 2230 can be inserted over the top of an extending over a portion of the lower portion 2232 (see FIG. 22) and may be referred to as a "top hat" design. In FIG. 23, the upper portion 2230 is lifted off of the lower portion 2232 to reveal an opening or access to a volume 2208 of the integrating optical system. In the open position, the chamber walls are visible (e.g., formed by side, top and bottom panels covered with diffuse reflective material 210). Also shown are support wires 2254 extending from one wall to an opposite wall to support an object to be treated within the volume 2208. In this case, the support wires support a light transmissive plate 2256 (or shelf) that assists in supporting the object. Also shown are bushing assemblies 2250 each having a channel 2252. In the open position, an object is placed on the plate 2256. For example, a portion of a catheter is be cured is placed on the plate 2256 with the ends extending out of the chamber via the channels 2252. The upper portion 2230 is inserted over the lower portion 2232 to complete the treatment volume 2208. Light shields 2234 are formed in the upper portion 2230 to cover the bushing assemblies 2250 and block at least some light from exiting the volume 2208 during treatment. Aside from the alternative removable coupling of the upper and lower portions and the varied bushing assembly design, the embodiment of FIGS. 22-24 functions similarly to the embodiment of FIGS. 4-9 and this description is not repeated. That is, this embodiment is coupled to an external light source assembly using a light guide 414 and allows for easy, safe, consistent and uniform treatment of small, heat sensitive objects with light.

Figure 24:
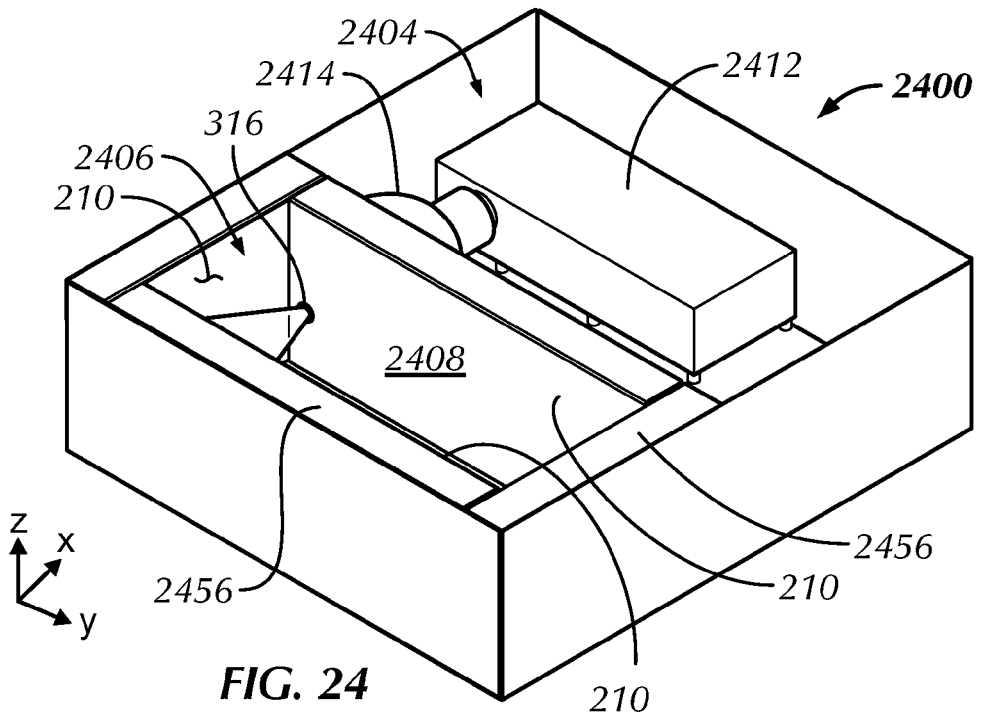
FIG. 24 is a first top perspective view of an integrating optical system comprising an integrating optical chamber and an integrated light source in accordance with several embodiments.
Figure 25:
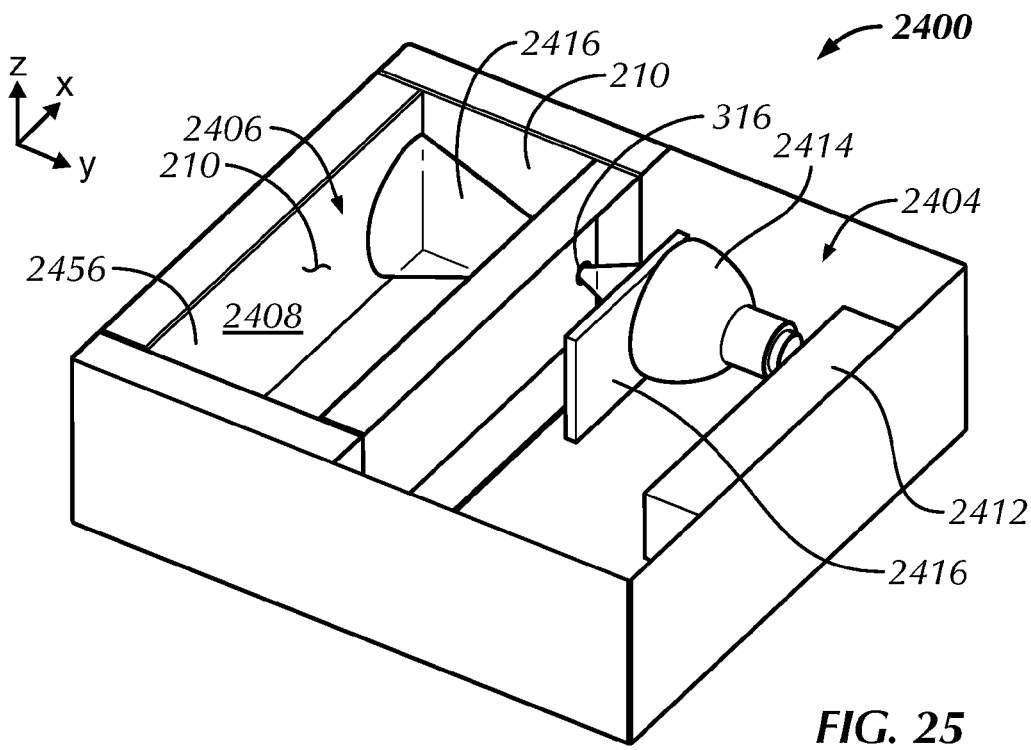
FIG. 25 is a second top perspective view of the integrating optical system of FIG. 24 in accordance with several embodiments.
Figure 26:
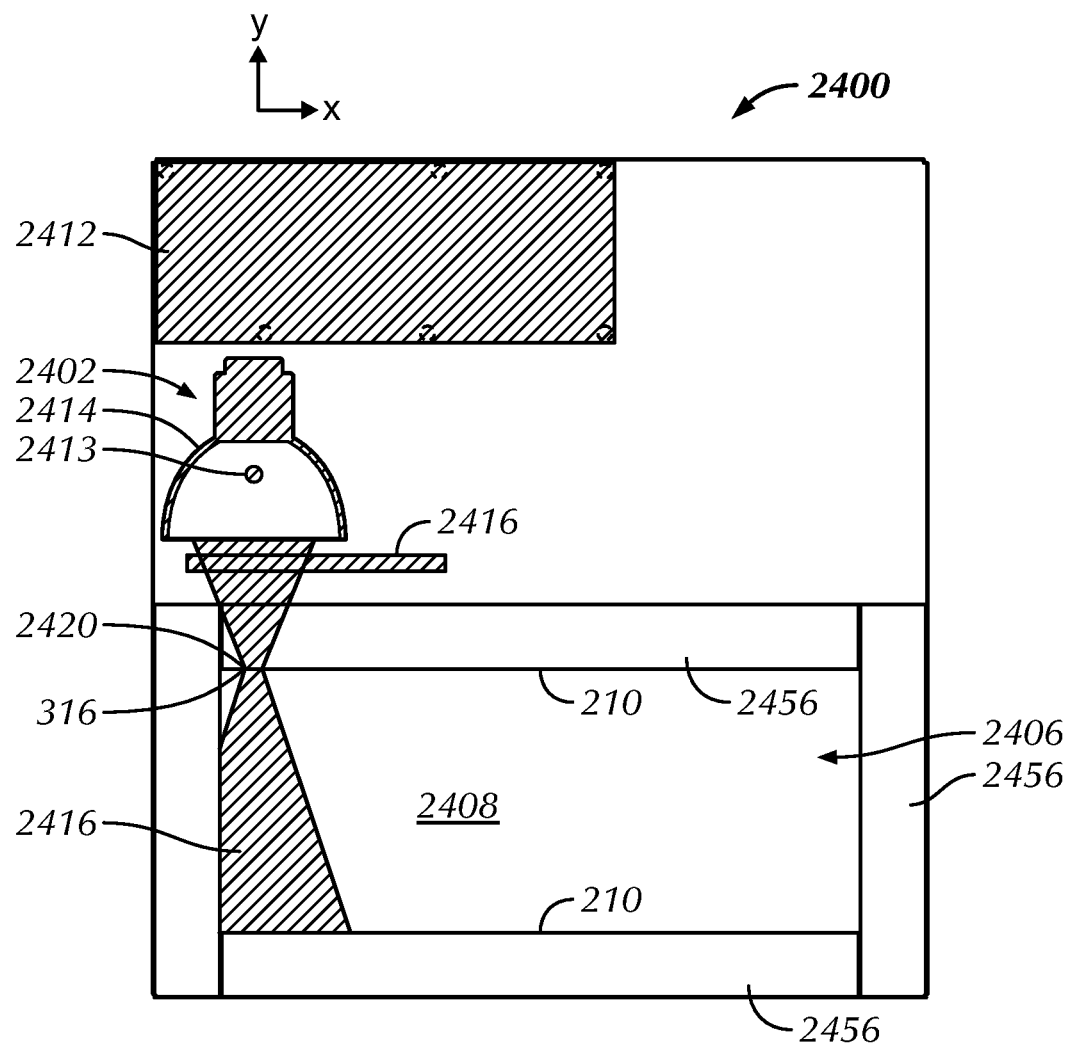
FIG. 26 is a top plan schematic view of the integrating optical system of FIG. 24 in accordance with several embodiments.

Referring next to FIGS. 24-26, different views are shown of an integrating optical system 2400 having an integrated light source assembly 2404 in accordance with several embodiments. For example, the embodiments of FIGS. 24-26 are several embodiments of the integrating optical system of FIG. 3, for example. In this embodiment, the light source assembly 2404 includes a light source 2413, a reflector assembly 2414, a light source power supply 2412, and a shutter, variable aperture and/or filter 2416. An integrating optical chamber 2408 includes chamber walls 2456, at least a portion of which are covered in diffuse reflective material 210, the walls forming a treatment volume 2408. An aperture 316 is formed in a wall to couple light from the light source 2413 to the volume 2408. Also illustrated is that the reflector assembly and/or other optical components of the light source assembly 2404 are designed to focus the light from the light source 2413 to a focal plane 2420 at or near the aperture 316 such that the aperture may be made small. This results in the efficient transfer of light into the volume 2408 having an input light cone 2416. Operation of the system of FIGS. 24-26 is similar that of other systems described herein.

Figure 27:
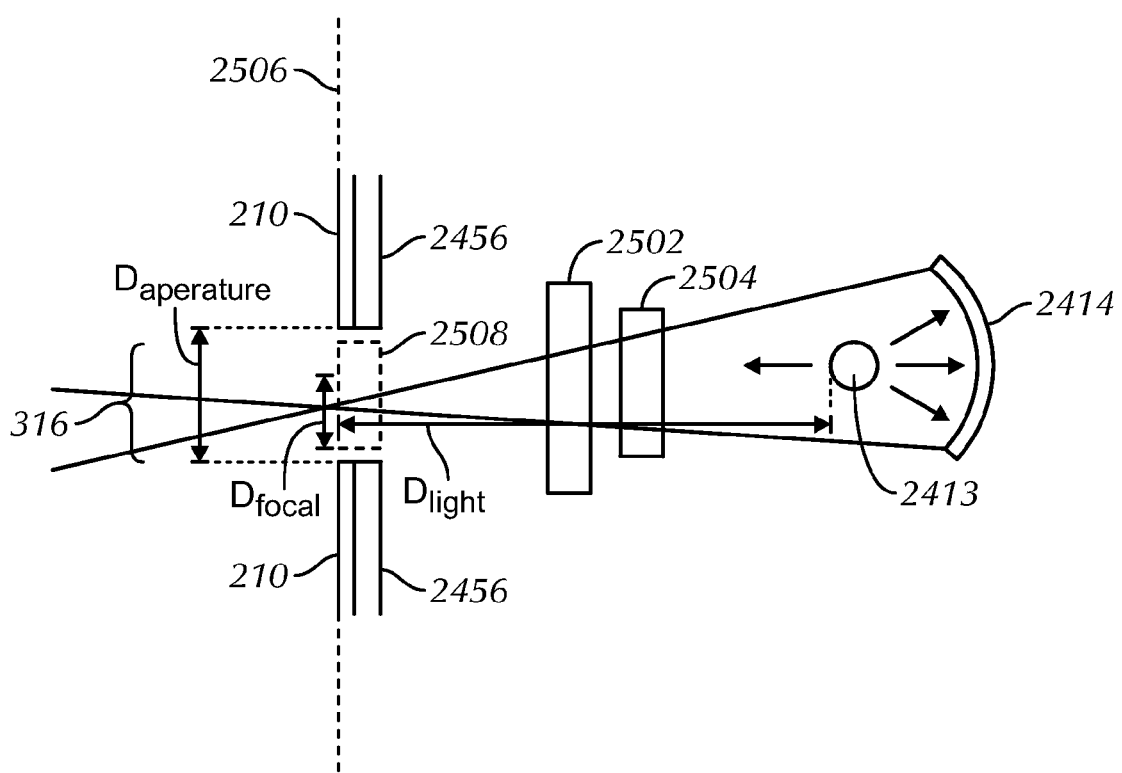
FIG. 27 is a side elevation schematic view of the integrated coupling of a light source assembly to an integrating optical chamber of an integrating optical system in accordance with several embodiments.

FIG. 27 is a side elevation schematic view of the integrated coupling of a light source assembly to an integrating optical chamber of an integrating optical system in accordance with several embodiments. This illustration better illustrates embodiments for coupling the light source to the integrating optical chamber. This illustration includes many of the components of FIGS. 24-26 and also includes an optional light transmissive window 2508 (e.g., quartz window), shutter/variable aperture 2502, optional filter 2504 (e.g., to pass or block one or more desired wavelengths), a focal plane 2506, a diameter ($D_{focal}$) of the light at the focal plane or focal spot and a diameter ($D_{aperture}$) of the aperture 316. In order to minimize the size of the aperture to optimize the amount of light entering the volume 2408 and integrating therein, the reflector assembly 2414 and any other optical components, lens, etc, are configured to focus the light to a focal spot or on a focal plane that is aligned to the plane of the aperture. It is understood that the focal plane 2506 is preferred to be aligned with the aperture plane, however, in some embodiments, good results are achieved when the focal plane is no more than 25 percent of the distance from the light source to the aperture, $D_{light}$ offset from the aperture plane. In some embodiments, the diameter of the aperture $D_{aperture}$ is configured to be no more than 1 to 5 times the diameter of the focal spot ($D_{focal}$).

FIG. 28 is a flowchart illustrating a method for use in calibrating an uncalibrated light sensor for use in an integrating optical system in accordance with several embodiments. In some embodiments, this method may be performed to calibrate a sensor for use in one or more of the integrating optical systems described herein or other optical systems. Initially, diffusely reflected light is providing within an integrating optical chamber (Step 2802). An amount of the diffusely reflected light is measured at a surface of the chamber using a calibrated light sensor (such as a radiometer or spectrometer) for at least one wavelength of interest (Step 2804). The wavelengths of interest may be a narrow group or range of wavelengths or may be a larger or wider band of wavelengths. For example, the calibrated light sensor may be a commercially available, self powered sensor that may simply be positioned in the chamber in a location where it will not received direct light rays from the light source. Feedback signals from known sensors are usually a voltage derived from a photodiode whose output is proportional to the incident optical power. In some embodiments, the sensed voltage is to be related to the exitance of the chamber walls in watts per unit area. In one embodiment, the measured value of the wall exitance is expressed as "$E_{CAL}$".

Then, an amount of the diffusely reflected light is measured at a surface of the chamber using an un-calibrated light sensor at the wavelength/s of interest (Step 2806). This step may be performed concurrently with Step 2804, or before or after Step 2804 so long as the conditions and light treatment is substantially the same. In one embodiment, the measured value output of an uncalibrated photodiode sensor being used is expressed as "$V_{PD}$".

Next, a calibration factor is determined based on the measurements from the calibrated and un-calibrated light sensors (Step 2808). In some embodiments, the calibration factor is determined as the ratio of the two ($E_{CAL}/V_{PD}$). This calibration value is recorded in controller memory. During treatment or cure, the object incidence is the product of sensor output and calibration factor. In one case, the dose is the time integral of the sensor output and calibration factor product.

These embodiments assume a linear response in the un-calibrated sensor. If the response is nonlinear, multiple measurements are taken at several different irradiance levels and used to determine a calibration factor.

In some embodiments of an integrating optical system which is coupled to a non-integrated light source, e.g., using a light guide, one or more of the following features may be implemented in such system. In some embodiments, a curing chamber is provided that that is small enough to fit on an assembly bench station (chamber volume of ~36 cu. in.), yet still provides the cure uniformity advantages of a much larger integrating sphere type curing chamber. In some embodiments, an entire device can be cured at once with no rotation or movement of the part or source. In some embodiments, a curing system comprises a diffuse reflecting chamber, a way to open the chamber to insert, assemble, apply coatings or adhesives or other UV curable features, and remove objects, and an input light port located such that no rays from the light source strike the object directly. In some embodiments, an intense UV curing chamber and supporting/containing structures also protects the operator from dangerous UV exposure, yet allows the operator to rapidly open and close the chamber, insert and remove objects, assemble parts, apply adhesives, coatings or other UV curable features. Other UV curing systems require much more operator time and effort to open, close and manipulate, a light shield that must be removed and replaced, eye protection, and the like.

In some embodiments, a way is provided to hold or suspend or fixture the object inside the chamber for assembly, adhesive dispensing and curing wherein object motion is not required. In some embodiments, the object is held so that it simultaneously securely holds the part, does not obstruct light reaching the area to be cured, does not absorb significant light and reduce the efficiency of the chamber, and/or can be opened and closed rapidly and easily by the operator.

In some embodiments, a means is provided for curing a small area of an extended object by letting the portions of the object that don't need curing extend out of the chamber in a manner that has minimal impact on the chamber performance. In some embodiments, an adhesive dispensing means suspended above chamber so that once parts are assembled, the dispensing means may be lowered in place for controlled dispensing of adhesive onto the object. In some embodiments, a video camera may be suspended above chamber to provide magnified view of parts during assembly and dispensing. The camera may display its image on the control system user interface.

In some embodiments, high uniformity irradiance over device's extended three dimensional surfaces is provided during cure while using a small, single source such as short arc lamp, light guide or LED. In some embodiments, high uniformity irradiance is provided with a single light source inputting light into the chamber (in other words, furcated light guides not needed).

In some embodiments, a light source already owned by the operator may be used, thereby eliminating the cost of purchase of a separate UV light source. In some embodiments, a system may be used for a variety of applications or devices and reduces fixturing costs. Conventional methods must be adjusted for each different device being cured. For example, using conventional methods, a balloon catheter and a Y-connector on IV tubing require different fixturing and equipment.

In some embodiments, spatial dependence between light source and device being cured is eliminated by integrating input light. In some embodiments, heating of part is reduced due to uniformity of radiation. In some embodiments, irradiance at object with object in place is measurable. In some embodiments, a single fixture for device assembly, dispensing UV curable material and curing is provided. In some embodiments, an inert gas such as nitrogen or $CO_2$ may be used due to the closed nature of several embodiments of the chamber.

Additionally, in embodiments that integrated the light source assembly and the chamber, lamp output is focused on chamber interior wall surface (thru a hole in the wall) to minimize losses and improve irradiance on object. This eliminates the light guide with its associated costs, optical losses and poor repeatability/reliability. In some embodiments, the light source, curing chamber and part fixturing are integrated. In some embodiments, a feedback control system controls dose delivered to part (rather than power applied) based on actual irradiance delivered to part measured during cure. In some embodiments, a feedback control system adjusts lamp output to compensate for degradation of output over lamp lifetime.

Exemplary Tests

Various exemplary integrating optical systems were tested as follows. A system similar to the embodiment of FIGS. 4-9 having a hinged design was tested having a 4"×3"×3" (L×W×H) chamber. Using an EFOS, Inc., spot cure system (100 W bulb, model number 100SS) with a Lumatec 5 mm light guide, the chamber wall exitance is 0.7 W/cm². A 0.5" diameter drop of Loctite 3311 adhesive on a quartz plate cured within 10 seconds. This setup successfully adhered a Y-hub to IV tubing using the Loctite 3311 adhesive in less than 10 seconds.

A system similar to the embodiment of FIGS. 22-23 having a top hat design was tested having a 3"×3"×3" (L×W×H) chamber. Using an EFOS spot cure system (100 W bulb, model number 100SS) with a Lumatec 5 mm light guide, the chamber wall exitance is 1.1 W/cm². A 0.5" diameter drop of Loctite adhesive on a quartz plate cures within 5 seconds. This setup successfully adhered a Y-hub to IV tubing using the Loctite 3311 adhesive in 5 seconds.

While the invention herein disclosed has been described by means of specific embodiments, examples and applications thereof, numerous modifications and variations could be made thereto by those skilled in the art without departing from the scope of the invention set forth in the claims.

What is claimed is:

1. An integrating optical system, comprising:
   a housing having a first portion and a second portion, the first portion being coupled to the second portion;
   a chamber having a volume and formed within the first portion and the second portion when coupled together, the chamber comprising a diffuse reflective material, wherein the first portion is separable from the second portion to allow insertion and removal of at least one light treatable object in and out of the chamber;
   at least one aperture formed in the chamber configured to couple to a light source and oriented to direct light from the light source to at least a first portion of the diffuse reflective material; and
   at least one holding structure coupled to the chamber and configured to support the at least one light treatable object within the volume at a location, wherein the diffuse reflective material, the at least one aperture and the location ensure that the light from the light source is diffusely reflected by at least one portion of the diffuse reflective material to integrate the light within the volume and impact the at least one light treatable object with substantially uniform light without movement of the at least one light treatable object.

2. The system of claim 1, wherein the first portion is coupled to the second portion by at least one hinge.

3. The system of claim 1, wherein the first portion is sized to be vertically placed over the top of the second portion so that the first portion is slidably coupled to the second portion.

4. The system of claim 1, wherein the holding structure comprises at least one guide piece.

5. The system of claim 4, wherein a second portion of the diffuse reflective material covers a portion of the at least one guide piece.

6. The system of claim 4, wherein the at least one guide piece comprises at least one channel configured to support a portion of the at least one light treatable object.

7. The system of claim 1, further comprising at least two support panels, wherein a portion of a first piece of the diffuse reflective material and a portion of a second piece of the diffuse reflective material are pressed together between the at least two support panels.

8. The system of claim 1, further comprising a light sensor coupled to the chamber configured to sense an amount of diffusely reflected light at a location within the chamber.

9. The system of claim 8, wherein a field of view of the light sensor does not include any light rays directly from the light source.

10. The system of claim 1, wherein the holding structure comprises one or more of: one or more wires; one or more rods; one or more stands; one or more guide pieces, and one or more bushing assemblies.

11. The system of claim 1, wherein the holding structure is at least partially light transmissive.

12. The system of claim 1, wherein the light source comprises one or more of: a discharge lamp, a microwave-excited arc lamp, an electrodeless arc lamp, a low pressure arc lamp, a medium pressure arc lamp, a high pressure arc lamp, an incandescent lamp, an infrared (IR) light source, an ultraviolet (UV) light source, a visible light source, a light emitting diode, and a laser.

13. The system of claim 1, wherein the integrating optical system is configured for operation such that the substantially uniform light is used for one or more of UV, IR or thermal curing of the light treatable object and sterilization of at least one surface of the light treatable object.

14. A method of treating at least one treatable object, comprising:
    providing light, through an aperture, within a chamber from at least one light source, wherein the chamber has a volume and is formed within a first portion and a second portion of a housing when the first portion and second portion are coupled together, wherein the first portion is separable from the second portion to allow insertion and removal of the at least one light treatable object in and out of the chamber, wherein the chamber further comprises a diffuse reflective material; and
    diffusely reflecting the light from at least a first portion of the diffuse reflective material so that the light from the at least one light source is integrated within the volume and impacts the at least one light treatable object being supported by at least one holding structure with substantially uniform light without movement of the light treatable object.

15. The method of claim 14, further comprising sensing an amount of diffusely reflected light within the volume.

16. The method of claim 15, further comprising determining a feedback parameter based on the sensed amount of diffusely reflected light.

17. The method of claim 16 further comprising adjusting the irradiance inside the chamber based at least in part on the feedback parameter in order to adjust the substantially uniform light incident on the light treatable object.

18. The method of claim 16 wherein the adjusting the irradiance step comprises adjusting a time duration that the light is provided through the aperture to adjust a dose of the light incident on the light treatable object.

19. The method of claim 16 wherein the adjusting the irradiance step comprises adjusting an amount of light provided through the aperture.

20. The method of claim 19 wherein the adjusting the irradiance step comprises adjusting one or more of: a parameter of the light treatment; a power of the at least one light source; a power of the light provided through the aperture after produced by the at least one light source; a wavelength of the light provided through the aperture; a loss area within the chamber; and an open area on the chamber surface.

21. The method of claim 14, further comprising curing the light treatable object with the substantially uniform light.

22. The method of claim 14, further comprising sterilizing at least one surface of the light treatable object with the substantially uniform light.

23. The method of claim 14, further comprising placing the at least one treatable object in at least one guide piece comprising at least one channel.

24. The method of claim 19, wherein a second portion of the diffuse reflective material covers a portion of the at least one guide piece.

25. A method for use with an integrating optical device, comprising:
    measuring an amount of diffusely reflected light at a surface within a chamber;
    establishing, based on the amount of the diffusely reflected light, a feedback parameter that is proportional to an irradiance of at least one light treatable object within the chamber, the diffusely reflected light being integrated within the chamber to provide the irradiance comprising substantially uniform light; and adjusting the irradiance in the chamber from at least one light source based on the feedback parameter.

26. The method of claim 25 further comprising:

measuring a first amount of the diffusely reflected light at a first surface of the chamber using a calibrated light sensor at least one wavelength of interest;

measuring a second amount of the diffusely reflected light at the surface of the chamber using an un-calibrated light sensor at the at least one wavelength of interest; and determining a calibration factor based on the measurements from the calibrated and un-calibrated light sensors.

27. An integrating optical system, comprising:

a housing comprising a first portion and a second portion, the first portion being coupled to the second portion;

a chamber having a volume and formed within the first portion and the second portion when coupled together, the chamber comprising a diffuse reflective material;

at least one aperture formed in the chamber;

a third portion of the housing; and at least one light source integrated within the third portion of the housing and configured such that light from the light source is focused at or near the aperture and a diameter of the aperture is no more than 5 times a diameter of a focal spot of the light, wherein the light is oriented to impact at least a portion of the diffuse reflective material, and wherein the diffuse reflective material and the at least one aperture ensure that the light from the light source is diffusely reflected by at least one portion of the diffuse reflective material to integrate the light within the volume and impact a light treatable object located within the volume with substantially uniform light without movement of the light treatable object.

* * * * *

UNITED STATES PATENT AND TRADEMARK OFFICE
CERTIFICATE OF CORRECTION

PATENT NO. : 8,426,800 B2  
APPLICATION NO. : 13/229544  
DATED : April 23, 2013  
INVENTOR(S) : Ingram et al.

Page 1 of 1

It is certified that error appears in the above-identified patent and that said Letters Patent is hereby corrected as shown below:

In the claims:

Claim 26, Column 29, Line 10; before the words "at least" insert the word -- at --.

Signed and Sealed this  
Sixth Day of August, 2013

Teresa Stanek Rea  
*Acting Director of the United States Patent and Trademark Office*